(12) United States Patent
Stanford et al.

(10) Patent No.: US 8,252,761 B2
(45) Date of Patent: Aug. 28, 2012

(54) METHOD OF INCREASING MURINE ES CELL DIFFERENTIATION WITH PCL2

(75) Inventors: William L. Stanford, Toronto (CA); Emily Walker, Toronto (CA); Wing Y. Chang, Toronto (CA)

(73) Assignee: Ottawa Hospital Research Institute, Ottawa (CA)

( * ) Notice: Subject to any disclaimer, the term of this patent is extended or adjusted under 35 U.S.C. 154(b) by 296 days.

(21) Appl. No.: 12/457,407

(22) Filed: Jun. 10, 2009

(65) Prior Publication Data

US 2010/0298406 A1   Nov. 25, 2010

Related U.S. Application Data

(60) Provisional application No. 61/129,191, filed on Jun. 10, 2008.

(51) Int. Cl.
*A61K 48/00* (2006.01)
*C12N 15/74* (2006.01)

(52) U.S. Cl. ...................................... 514/44 R; 435/476

(58) Field of Classification Search .................. None
See application file for complete search history.

(56) References Cited

OTHER PUBLICATIONS

Furue, et al. (2005) In Vitro Cellular and Developmental Biology—Animal, 41:19-28.*
Canman, et al. (1995) Genes & Development, 9: 600-611.*
Yang, et al. (2004) Oncogene, 23: 2096-2106.*
Measday, et al. (1994) Science, 266: 1391-95.*
Wilson, et al. (2004) "c-Myc Controls the Balance Between Hematopoietic Stem Cell Self-Renewal and Differentiation", Genes a& Development, 25(24): 2747-63.*
Alon, (2007) Network motifs: theory and experimental approaches. Nature Reviews, vol. 8, p. 450-461.
Ambrosetti, et al., (1997) Synergistic Activation of the Fibroblast Growth Factor 4 Enhancer by Sox2 and Oct-3 Depends on Protein-Protein Interactions Facilitated by a Specific Spatial Arrangement of Factor Binding Sites. Molecular and Cellular Biology, vol. 17, p. 6321-6329.
Beissbarth, et al. (2004) GOstat: find statistically overrepresented Gene Ontologies within a group of genes. Bioinformatics (Oxford, England) vol. 20 No. 9, pp. 1464-1465.
Bernstein, et al. (2006) A Bivalent Chromatin Structure Marks Key Developmental Genes in Embryonic Stem Cells. Cell vol. 125, p. 315-326.
Boyer, et al. (2006) Polycomb complexes repress developmental regulators in murine embryonic stem cells. Nature, vol. 441, p. 349-353.
Cao, et al. (2002) Role of Histone H3 Lysine 27 Methylation in Polycomb-Group Silencing. Science 298, p. 1039-1043.
Chamberlain, et al. (2008) Polycomb Repressive Complex 2 Is Dispensable for Maintenance of Embryonic Stem Cell Pluripotency. Stem Cells 2008;26:1496-1505.
Chambers, et al. (2003) Functional Expression Cloning of Nanog, a Pluripotency Sustaining Factor in Embryonic Stem Cells. Cell, vol. 113, p. 643-655.
Chambers, et al. (2007) Nanog safeguards pluripotency and mediates germline development. Nature, vol. 450, p. 1230-1235.
Czermin, et al. (2002) *Drosophila* Enhancer of Zeste/ESC Complexes Have a Histone H3 Methyltransferase Activity that Marks Chromosomal Polycomb Sites. Cell, vol. 111, p. 185-196.
Davey, et al. (2006) Spatial Organization of Embryonic Stem Cell Responsiveness to Autocrine Gp130 Ligands Reveals an Autoregulatory Stem Cell Niche. Stem Cells 2006;24:2538-2548.
Deng, et al. (2009) Unifying Fluorescence Microscopy and Mass Spectrometry for Studying Protein Complexes in Cells. Molecular & Cellular Proteomics 8.6, p. 1413-1423.
Dignam, et al. (1983) Accurate transcription initiation by RNA polymerase II in a soluble extract from isolated mammalian nuclei. Nucleic Acids Research, vol. 11 No. 5, p. 1475-1489.
Duncan (1982) Polycomblike: A Gene That Appears to Be Required for the Normal Expression of the Bithorax and Antennapedia Gene Complexes of *Drosophila* Melanogaster. Genetics 102: 49-70.
Evans, et al. (1981). Establishment in culture of pluripotential cells from mouse embryos. Nature 292, 154-156.
Faust et al. (1995). The *eed* mutation disrupts anterior mesoderm production in mice. Development (Cambridge, England) 121, 273-285.
Furuyama, et al. (2003). Polycomb group proteins ESC and E(Z) are present in multiple distinct complexes that undergo dynamic changes during development. Genesis 35, 114-124.
Guo, et al. (2009). Klf4 reverts developmentally programmed restriction of ground state pluripotency. Development (Cambridge, England) 136, 1063-1069.
Hanna, et al. (2002). Requirement for *Foxd3* in maintaining pluripotent cells of the early mouse embryo. Genes & Development 16, 2650-2661.
Ivanova, et al. (2006). Dissecting self-renewal in stem cells with RNA interference. Nature 442, 533-538.
Johnson, et al. (2007). Genome-wide mapping of in Vivo protein-DNA interactions. Science (New York, NY 316, 1497-1502.
Kaji, et al. (2006). The NuRD component Mbd3 is required for pluripotency of embryonic stem cells. Nature Cell Biology 8, 285-292.
Kim, et al. (2008). An extended transcriptional network for pluripotency of embryonic stem cells. Cell 132 , 1049-1061.
Kim, et al. (2009). AEBP2 as a potential targeting protein for Polycomb Repression Complex PRC2. Nucleic Acids Research.
Kitaguchi, et al. (2001). *Xenopus Polycomblike 2 (XPcl2)* controls anterior to posterior patterning of the neural tissue. Development Genes and Evolution 211, 309-314.
Ku, et al. (2008). Genomewide analysis of PRC 1 and PRC2 occupancy identifies two classes of bivalent domains. PLoS Genetics 4, el000242.
Kunath, et al. (2003). Transgenic RNA interference in ES cell-derived embryos recapitulates a genetic null phenotype. Nat Biotechnol 21,559-561.

(Continued)

*Primary Examiner* — Robert M Kelly

(57) ABSTRACT

A method of suppressing undesirable cell proliferation, such as tumor growth, is provided comprising the step of increasing the level of PCL2 in target cells.

3 Claims, 17 Drawing Sheets

OTHER PUBLICATIONS

Kuzmichev, et al. (2002). Histone methyltransferase activity associated with a human multiprotein complex containing the Enhancer of Zeste protein. Genes & Development 16, 2893-2905.

Kuzmichev, et al. (2005). Composition and histone substrates of polycomb repressive group complexes change during cellular differentiation. Proceedings of the National Academy of Sciences of the United States of America 102,1859-1864.

Lee, et al. (2006). Control of developmental regulators by Polycomb in human embryonic stem cells. Cell 125, 301-313.

Loh, et al. (2006). The Oct4 and Nanog transcription network regulates pluripotency in mouse embryonic stem cells. Nat Genet 38, 431-440.

Lund, et al. (2004). Polycomb complexes and silencing mechanisms. Current Opinion in Cell Biology 2004, 16:239-246.

Martin, (1981). Isolation of a pluripotent cell line from early mouse embryos cultured in medium conditioned by teratocarcinoma stem cells. Proceedings of the National Academy of Science, USA, vol. 78, No. 12, pp. 7634-7638.

Mitsui, et al. (2003). The Homeoprotein Nanog Is Required for Maintenance of Pluripotency in Mouse Epiblast and ES Cells. Cell, vol. 113, 631-642, May 30, 2003.

Morrison, et al. (2006). Conserved roles for Oct4 homologues in maintaining multipotency during early vertebrate development. Development 133, 2011-2022.

Nekrasov, et al. (2007). Pcl-PRC2 is needed to generate high levels of H3-K27 trimethylation at Polycomb target genes. The EMBO Journal (2007) 26, 4078-4088.

Nichols, et al. (1998). Formation of Pluripotent Stem Cells in the Mammalian Embryo Depends on the POU Transcription Factor Oct4. Cell, vol. 95, 379-391.

Niwa, et al. (2000). Quantitative expression of Oct-3/4 defines differentiation, dedifferentiation or self-renewal of ES cells. Nature Genetics, vol. 24, 372-376.

Niwa, et al. (2009). A parallel circuit of LIF signalling pathways maintains pluripotency of mouse ES cells. Nature Genetics, vol. 460, 118-122.

O'Carroll, et al. (2001). The *Polycomb*-Group Gene *Ezh2* Is Required for Early Mouse Development. Molecular and Cellular Biology, Jul. 2001, vol. 21, No. 13, p. 4330-4336.

O'Connell, et al. (2001). Polycomblike PHD Fingers Mediate Conserved Interaction with Enhancer of Zeste Protein. The Journal of Biological Chemistry, vol. 276, No. 46, Issue of Nov. 16, pp. 43065-43073.

Oktaba, et al. (2008). Dynamic Regulation by Polycomb Group Protein Complexes Controls Pattern Formation and the Cell Cycle in *Drosophila*. Developmental Cell 15, 877-889.

Pasini, et al. (2004). Suz12 is essential for mouse development and for EZH2 histone methyltransferase activity. The EMBO Journal (2004) 23, 4061-4071.

Pasini, et al. (2007). The Polycomb Group Protein Suz12 Is Required for Embryonic Stem Cell Differentiation. Molecular and Cellular Biology, May 2007, p. 3769-3779.

Peerani, et al. (2009). Patterning Mouse and Human Embryonic Stem Cells Using Micro-contact Printing. Stem Cells in Regenerative Medicine, Methods and Protocols, vol. 482, 21-33.

Remondelli, et al. (1997) Interactions of the zinc-regulated factor (ZiRF1) with the mouse metallothionein Ia promoter. Biochem. J. 323, 79-85.

Remondelli, et al. (1997) Regulation of ZiRF1 and basal SP1 transcription factor MRE-binding activity by transition metals. FEBS Letters 416, 254-258.

Rodda, et al. (2005) Transcriptional Regulation of *Nanog* by OCT4 and SOX2. The Journal of Biological Chemistry. vol. 280, No. 26, Issue of Jul. 1, pp. 24731-24737.

Salva, et al. (2008) Recruitment of *Drosophila* Polycomb-group proteins by Polycomblike, a component of a novel protein complex in larvae. Development 135, 813-817.

Schuettengruber, et al. (2007) Genome Regulation by Polycomb and Trithorax Proteins. Cell 128, 735-745, Feb. 23, 2007.

Schwartz, et al. (2007) Polycomb silencing mechanisms and the management of genomic programmes. Nature Reviews—Genetics. vol. 8, 9-22.

Shen et al. (2008) EZH1 Mediates Methylation on Histone H3 Lysine 27 and Complements EZH2 in Maintaining Stem Cell Identity and Executing Pluripotency. Molecular Cell 32, 491-502, Nov. 21, 2008.

Shevchenko et al. (1996) Mass Spectrometric Sequencing of Proteins from Silver-Stained Polyacrylamide Gels. Anal. Chem. 1996, 68, 850-858.

Silva, et al. (2003) Establishment of Histone H3 Methylation on the Inactive X Chromosome Requires Transient Recruitment of Eed-Enx1 Polycomb Group Complexes. Developmental Cell, vol. 4, 481-495, Apr. 2003.

Singla, et al. (2010), Floxin, a resource for genetically engineering mouse ESCs. Nature Methods, vol. 7. No. 1, 50-54.

Smith et al. (1987) Buffalo Rat Liver Cells Produce a Diffusible Activity Which Inhibits the Differentiation of Murine Embryonal Carcinoma and Embryonic Stem Cells. Developmental Biology 121,1-9.

Smith et al. (1988) Inhibition of pluripotential embryonic stem cell differentiation by purified polypeptides. Nature, vol. 336, 688-690.

Takahashi, et al. (2006) Induction of Pluripotent Stem Cells from Mouse Embryonic and Adult Fibroblast Cultures by Defined Factors. Cell 126, 663-676, Aug. 25, 2006.

Tie, et al. (2003) A 1-Megadalton ESC/E(Z) Complex from *Drosophila* That Contains Polycomblike and RPD3. Molecular and Cellular Biology, vol. 23, No. 9, May 2003, p. 3352-3362.

Walker, et al. (2007) Prediction and Testing of Novel Transcriptional Networks Regulating Embryonic Stem Cell Self-Renewal and Commitment. Cell Stem Cell 1, 71-86, Jul. 2007.

Walker, et al. (2010) Polycomb-like 2 Associates with PRC2 and Regulates Transcriptional Networks during Mouse Embryonic Stem Cell Self-Renewal and Differentiation. Cell Stem Cell 6, 153-166, Feb. 5, 2010.

Wang, et al. (2004) Chick Pcl2 regulates the left-right asymmetry by repressing Shh expression in Hensen's node. Development and Disease vol. 131, 4381-4391.

Wang, et al. (2007) Polycomblike-2-Deficient Mice Exhibit Normal Left-Right Asymmetry. Developmental Dynamics, vol. 236:853-861.

Williams et al. (1988) Myeloid leukaemia inhibitory factor maintains the developmental potential of embryonic stem cells. Nature vol. 336, 684-687.

Woltjen, et al. (2009) piggyBac transposition reprograms fibroblasts to induced pluripotent stem cells Naturel vol. 458|Apr. 9, 2009 766-771.

Yi, et al. (2008) Tcf3 Functions as a Steady-State Limiter of Transcriptional Programs of Mouse Embryonic Stem Cell Self-Renewal. Stem Cells 2008;26:1951-1960.

Ying, et al. (2003) BMP Induction of Id Proteins Suppresses Differentiation and Sustains Embryonic Stem Cell Self-Renewal in Collaboration with STAT3. Cell, vol. 115, pp. 281-292, Oct. 31, 2003.

Ying, et al. (2003) Conversion of embryonic stem cells into neuroectodermal precursors in adherent monoculture. Nature vol. 21, pp. 183-186, Feb. 2003.

Yuan, et al. (1995) Developmental-Specific activity of the FGF-4 enhancer requires the synergistic action of Sox2 and Oct-3. Genes Dev. 1995 vol. 9: pp. 2635-2645.

Yun, et al. (2006) Genomic DNA functions as a universal external standard in quantitative real-time PCR. Nucleic Acids Research, 2006, vol. 34, No. 12 e85.

Zhang, et al. (2006) Zfp206 regulates ES cell gene expression and differentiation. Nucleic Acids Research, 2006, vol. 34, No. 17, pp. 4780-4790.

\* cited by examiner

A)

MRDSTGAGNSLVHKRSPLRRNQKTSASLNKLSLQDGHKAKKPACKFEEGQDVLARWSDGLFYLGTIKKIN
ILKQSCFIIFEDSSKSWVLWKDIQTGATGSGEMVCTICQEEYSEAPNEMVICDKCGQGYHQLCHTPHIDSSVI
DSDEKWLCRQCVFATTTKRGGALKKGPNAKALQVMKQTLPYSVADLEWDAGHKTNVQQCYCYCGGPG
DWYLKMLQCCKCKQWFHEACVQCLQKPMLFGDRFYTFICSVCSSGPEYLKRLPLQWVDIAHLCLYNLSVI
HKKKYFDSELELMTYINENWDRLHPGELADTPKSERYEHVLEALNDYKTMFMSGKEIKKKKHLFGLRIRV
PPVPPNVAFKAEKEPEGTSHEFKIKGRKASKPTSDSREVSNGIEKKGKKKSVGRPPGPYTRKMIQKTAELPL
DKESVSENPTLDLPCSIGRTEGIAHSSNTSDVDLTGASSANETTSASISRHCGLSDSRKRTRTGRSWPAAIPHL
RRRRGRLPRRALQTQNSEVVKDDEGKEDYQFEELNTEILNNLADQELQLNHLKNSITSYFGAAGRIACGEK
YRVLARRVTLDGKVQYLVEWEGATAS

B)

MRDSTGAGNSLVHKRSPLRRNQKTSASLNKLSLQDGHKAKKPACKFEEGQDVLARWSDGLFYLGTIKKIN
ILKQSCFIIFEDSSKSWVLWKDIQTGATGSGEMVCTICQEEYSEAPNEMVICDKCGQGYHQLCHTPHIDSSVI
DSDEKWLCRQCVFATTTKRGGALKKGPNAKALQVMKQTLPYSVADLEWDAGHKTNVQQCYCYCGGPG
DWYLKMLQCCKCKQWFHEACVQCLQKPMLFGDRFYTFICSVCSSGPEYLKRLPLQWVDIAHLCLYNLSVI
HKKKYFDSELELMTYINENWDRLHPGELADTPKSERYEHVLEALNDYKTMEVSNGIEKKGKKKSVGRPPG
PYTRKMIQKTAELPLDKESVSENPTLDLPCSIGRTEGIAHSSNTSDVDLTGASSANETTSASISRHCGLSDSRK
RTRTGRSWPAAIPHLRRRRGRLPRRALQTQNSEVVKDDEGKEDYQFEELNTEILNNLADQELQLNHLKNSI
TSYFGAAGRIACGEKYRVLARRVTLDGKVQYLVEWEGATAS

C)

MVCTICQEEYSEAPNEMVICDKCGQGYHQLCHTPHIDSSVIDSDEKWLCRQCVFATTTKRGGALKKGPNA
KALQVMKQTLPYSVADLEWDAGHKTNVQQCYCYCGGPGDWYLKMLQCCKCKQWFHEACVQCLQKPM
LFGDRFYTFICSVCSSGPEYLKRLPLQWVDIAHLCLYNLSVIHKKKYFDSELELMTYINENWDRLHPGELAD
TPKSERYEHVLEALNDYKTMFMSGKEIKKKKHLFGLRIRVPPVPPNVAFKAEKEPEGTSHEFKIKGRKASKP
TSDSREVSNGIEKKGKKKSVGRPPGPYTRKMIQKTAELPLDKESVSENPTLDLPCSIGRTEGIAHSSNTSDVD
LTGASSANETTSASISRHCGLSDSRKRTRTGRSWPAAIPHLRRRRGRLPRRALQTQNSEVVKDDEGKEDYQ
FEELNTEILNNLADQELQLNHLKNSITSYFGAAGRIACGEKYRVLARRVTLDGKVQYLVEWEGATAS

Figure 8

SEQUENCE LISTING

<160> NUMBER OF SEQ ID NOS: 48

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
agggaattgc acattcatcc                                               20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
cacaatgcct ggaaatgcta                                               20

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
cccgaagccc tccctaca                                                 18

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
tccttctcta gcccaagctg at                                            22

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
gcgtcaagag gcccatga                                                 18

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
ctgatctccg agttgtgcat ct                                            22

<210> SEQ ID NO 7
<211> LENGTH: 19
<212> TYPE: DNA

```
<213> ORGANISM: Artificial
<220> FEATURE:
<223> OTHER INFORMATION: primer

<400> SEQUENCE: 7
gtcctgcagc tcctgtctg                                                  19

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
cttggagccc agtgtagagg                                                 20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
ccaaagaggg gaagaaggtc                                                 20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
ctgtgtgagt tcgcaggtgt                                                 20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
gctgctgctc ttactgctga                                                 20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
ccagtttcag tccctgcttc                                                 20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
actgaaaaga caggccgaga                                                 20
```

```
<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
tgaacctggg taggaagtgg                                                   20

<210> SEQ ID NO 15
<211> LENGTH: 17
<212> TYPE: DNA
<213> ORGANISM: Artificial
<220> FEATURE:
<223> OTHER INFORMATION: primer

<400> SEQUENCE: 15
aaagcctcgc cggagaa                                                      17

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
agctgtccga gtccaaatcg                                                   20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
cacctcaact gcttcacctg                                                   20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
tgttctcttt ggcgacactg                                                   20

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
tcctccatgt gctgagactt gt                                                22

<210> SEQ ID NO 20
<211> LENGTH: 23
<212> TYPE: DNA
<213> ORGANISM: Artificial
<220> FEATURE:
<223> OTHER INFORMATION: primer
```

<400> SEQUENCE: 20
tgccactttg agcctagaag atc    23

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
cagcgtagca gaaggtgtga    20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
gccaggctgt catctatggt    20

<210> SEQ ID NO 23
<211> LENGTH: 23
<212> TYPE: DNA
<213> ORGANISM: Artificial
<220> FEATURE:
<223> OTHER INFORMATION: primer

<400> SEQUENCE: 23
agaagaaatg gcccactacc ttt    23

<210> SEQ ID NO 24
<211> LENGTH: 24
<212> TYPE: DNA
<213> ORGANISM: Artificial
<220> FEATURE:
<223> OTHER INFORMATION: primer

<400> SEQUENCE: 24
ccctctggtg actcatcttc attc    24

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
cacagagatc gtgctggaga    20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
tgtaccagcc ctcgtacttg    20

<210> SEQ ID NO 27
<211> LENGTH: 20
<212> TYPE: DNA

```
<213> ORGANISM: Artificial
<220> FEATURE:
<223> OTHER INFORMATION: primer

<400> SEQUENCE: 27
caaacgaaaa ggctcaggac                                                   20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
atgctctctg tgcgtctcct                                                   20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
gtggcgctta tcagaggaag                                                   20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
tttttccttg gcaagctgat                                                   20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
ttctggactc tccctgccta                                                   20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
gcacacttcc tcttcctcca                                                   20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
tgcaggacga tgaatctgag                                                   20
```

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
atactgtcag gggctggttg						20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
gaacgtacca ccaccaccat						20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
ccatgtaggg cgagtaggtc						20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
gagatgggac gggacactac						20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
ttgatgccgt tcatcttgtg						20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
gctccacaaa cgagaaaagc						20

<210> SEQ ID NO 40
<211> LENGTH: 20
<212> TYPE: DNA
<213> ORGANISM: Artificial
<220> FEATURE:
<223> OTHER INFORMATION: primer

```
<400> SEQUENCE: 40
agcaagggga aaaggacact                                           20

<210> SEQ ID NO 41
<211> LENGTH: 27
<212> TYPE: DNA
<213> ORGANISM: Artificial
<220> FEATURE:
<223> OTHER INFORMATION: primer

<400> SEQUENCE: 41
agtaacctag tcatggcaaa gaagatg                                   27

<210> SEQ ID NO 42
<211> LENGTH: 19
<212> TYPE: DNA
<213> ORGANISM: Artificial
<220> FEATURE:
<223> OTHER INFORMATION: primer

<400> SEQUENCE: 42
gggcctcaca ccctttctg                                            19

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
catcagccta cgacctcctc                                           20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
ggagtgagag tgctgggttc                                           20

<210> SEQ ID NO 45
<211> LENGTH: 23
<212> TYPE: DNA
<213> ORGANISM: Artificial
<220> FEATURE:
<223> OTHER INFORMATION: primer

<400> SEQUENCE: 45
ccctctggca ctgaggactt agt                                       23

<210> SEQ ID NO 46
<211> LENGTH: 28
<212> TYPE: DNA
<213> ORGANISM: Artificial
<220> FEATURE:
<223> OTHER INFORMATION: primer

<400> SEQUENCE: 46
cacaggtcaa gttatcaaag ctaagagt                                  28

<210> SEQ ID NO 47
<211> LENGTH: 20
<212> TYPE: DNA
```

-continued

```
<213> ORGANISM: Artificial
<220> FEATURE:
<223> OTHER INFORMATION: primer

<400> SEQUENCE: 47
tggagctgga gaaggagttt                                              20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
cagccagctc actttccctc                                              20
```

METHOD OF INCREASING MURINE ES CELL DIFFERENTIATION WITH PCL2

FIELD OF THE INVENTION

The present invention relates to methods of suppressing tumour growth.

BACKGROUND OF THE INVENTION

Embryonic stem cells (ESCs) are unspecialized cells that have the ability to self-renew, producing daughter cells with equivalent developmental potential, or to differentiate into more specialized cells. ESCs are derived from the inner cell mass of the pre-implantation embryo and are pluripotent, as they are able to differentiate in vivo into all cell types of the adult organism, but not into extraembryonic tissue. Control over cell fate decisions is accomplished through a variety of poorly defined molecular, genetic and epigenetic events.

Exogenous control of the pluripotent state can be achieved by a limited number of factors. When grown in fetal bovine serum (FBS)-containing medium and in the presence of murine embryonic fibroblast feeder cells or the cytokine leukemia inhibitory factor (LIF), mouse ESCs remain undifferentiated. LIF functions through the activation of gp130 signaling through binding to LIFRβ. LIFRβ then dimerizes with gp130 and transduces the signal through the JAK-STAT pathway and is thought to maintain the undifferentiated state through inhibition of mesoderm and endoderm formation. While STAT3 plays an important role in self-renewal of mouse ESCs, Stat3$^{-/-}$ embryos can undergo gastrulation, suggesting the existence of a STAT3-independent pathway for pluripotent stem cell self-renewal. Another factor, BMP4, provided by the serum, functions in the presence of LIF to maintain pluripotency by inducing phosphorylation and nuclear localization of Smad1, followed by up-regulation of Id proteins that block neural differentiation.

Three transcription factors are known to be critical in the establishment and/or maintenance of ESC pluripotency: Oct4, Nanog and Sox2. OCT4 (Pou5f1) has a highly conserved role in maintaining pluripotent cell populations and its expression level dictates ESC fate. SOX2 forms a complex with OCT4 and is necessary to co-operatively activate target genes in ESCs. These factors comprise one essential circuit regulating ESC pluripotency in which OCT4 regulates Sox2, and additionally, the OCT4-SOX2 complex activates Oct4 expression. Forced over-expression of Nanog maintains pluripotency and OCT4 levels in ESCs, even in the absence of LIF while it is itself regulated by OCT4 and SOX2. All three factors are down-regulated during differentiation induced by LIF withdrawal or retinoic acid (RA) induction. Genome-wide analysis of Oct4, Nanog, and Sox2 transcriptional targets illustrate that they regulate a plethora of genes implicated in numerous cellular pathways and functions. These genes along with c-myc and Klf4 play critical roles in the reprogramming of fibroblasts into induced pluripotent (iPS) cells. These same transcription factors are also implicated in tumour progression of cancers such as germ cell tumours, embryonal and breast carcinomas, and are currently being investigated as neoplastic markers.

Epigenetics refers to the acquisition of heritable traits that do not involve changes to the underlying genomic structure. Recent studies have revealed that epigenetic processes, such as DNA and histone methylation are also crucial determinants of cellular differentiation and help explain how the single genome of a stem cell can be actively modified to produce differentiated progeny with diverse cellular identities. The chromatin state or 'epigenome' of ESCs is largely void of DNA methylation but possesses histone modifications, in particular, methylation of histone H3 at lysine 4 (H3K4) and H3 at lysine 27 (H3K27). Di-methylation (2me-) at H3K4 is a transcriptionally active mark, whereas tri-methylation (3me-) of H3K27 is a repressive mark. This "bivalent" mark is believed to hold the chromatin in a transcriptionally ready state and upon specific stimulus the mark will be resolved as either activated or repressed, resulting in increased or decreased gene transcription.

The Polycomb group (PcG) proteins are regulators of the epigenetic state of the cell. These proteins exist in one of two main complexes, the maintenance complex Polycomb Repressive Complex 1 (PRC1) and the initiation complex Polycomb Repressive Complex 2 (PRC2). The core components of PRC2 are EED, EZH2 and SUZ12. Through the methyltransferase activity of the EZH2 protein, the PRC2 complex deposits the repressive mark of tri-methylation on lysine 27 of histone 3 (3me-H3K27). The PRC1 complex is thought to recognize the 3me-H3K27 histone modification and subsequently methylate the chromatin at that promoter to ensure stable, long-term silencing.

Ablation of PRC2 components results in embryonic lethality and defects in histone methylation and cell proliferation. Suz12-null ESCs are able to maintain an undifferentiated morphology but are unable to differentiate into mature cell types and maintain high levels of ESC markers even after the withdrawal of self-renewal signals. A recent report shows that Eed null ESCs express heightened levels of target differentiation genes but also maintain high levels of ESC markers and can be taken to high passage without losing their undifferentiated morphology. Ezh2, Eed, and Suz12 are downstream targets of the pRb/E2F pathway further indicating a role in proliferation and are up-regulated in cancers including lymphomas, prostate and breast cancers. Potential roles of PRC2 in tumorigenesis include suppression of cyclin-dependent kinase inhibitor p16ink4a expression and promoter hypermethylation.

Expression of PRC1 components, including Bmi1 and Mel18, is also deregulated in a number of tumour types. BMI1 possesses oncogenic properties when over-expressed and contributes to tumorigenesis by inhibiting expression of p16ink4a. In contrast, MEL18 appears to function as a tumour suppressor by repressing the expression of Bmi1 in breast cancer cells. Interestingly, BMI1 is required for maintenance of the hematopoietic and neural stem cell lineages and deletion of Bmi1 leads to pleiotropic defects and postnatal death by 20 weeks of age.

The highly conserved Pcl2 gene interacts with PRC2 by associating with EZH2 and plays a role in embryonic patterning in chick. The Pcl2 gene encodes a TUDOR domain and two plant homeodomain (PHD) type zinc fingers. The homeodomain PHD finger is found in nuclear proteins thought to be involved in chromatin-mediated transcriptional regulation. It is involved in protein-protein interaction and important for the assembly or activity of multicomponent complexes involved in transcriptional activation or repression. The TUDOR domain may bind to RNA or ssDNA or may control interactions with protein complexes.

In general, epigenetic alterations such as changes to DNA methylation and/or chromatin structure have been implicated in the pathogenesis and progression of neoplasia. Genome-wide DNA hypomethylation and regionalized promoter hypermethylation leads to genomic instability and repression of tumour-suppressor genes (TSGs), respectively, both hallmarks of cancers. The importance of epigenetic perturbations in neoplasia is highlighted by the fact that methylation and histone-modifying drugs have the capacity to inhibit malignancy in a number of cancer types. Importantly, tri-methylated H3K27 and di-methylated H3K9 are associated with gene promoters whose DNA is frequently hypermethylated and thus repressed in adult cancers.

The process of asymmetric stem cell division is highly regulated and perturbations in cell fate decisions can lead to a variety of disorders including developmental defects, degenerative disease and cancer. The identification of molecules with key roles in regulating ESC pluripotency is critical to provide an improved understanding of the molecular pathways responsible for maintenance of the stem cell phenotype. In addition, information regarding stem cell markers can be used to identify potential therapeutic targets.

It would be desirable, thus, to further understand the factors which control the pluripotent state.

SUMMARY OF THE INVENTION

It has now been found that Pcl2 plays a role in regulating embryonic and somatic stem cell fate, and in particular, expression of Pcl2 maintains normal cell differentiation, e.g. cell differentiation that occurs in healthy stem cells, thereby preventing tumour formation.

Thus, in one aspect of the present invention, a method of inhibiting, or at least reducing, undesirable cell proliferation and/or blockage of cell differentiation is provided comprising increasing the level of PCL2 within target cells to a level that prevents cell proliferation.

In another aspect, a method of preventing, or at least reducing, undesirable cell proliferation and/or blockage of cell differentiation is provided comprising increasing the expression of Pcl2 within target cells to a level that prevents cell proliferation.

A diagnostic method is also provided comprising the step of determining the level of Pcl2 expression in a biological sample obtained from a mammal, wherein detection of less than a normal level of Pcl2 expression is indicative of a condition in which there is abnormal cell activity.

In a further aspect of the invention, a method of preparing a population of undifferentiated stem cells is provided comprising inhibiting the expression Pcl2 in said stem cells.

These and other aspects of the invention will become apparent from the detailed description and figures which follow.

BRIEF DESCRIPTION OF THE DRAWINGS

FIG. 8 illustrates the amino acid sequences of three isoforms of PCL2 (A,B,C).

DETAILED DESCRIPTION OF THE INVENTION

A method of inhibiting, or at least reducing, undesirable cell proliferation and/or blockage of cell differentiation is provided comprising increasing the level of PCL2 within target cells, such as embryonic or somatic stem cells, to a normal level or to a level that prevents cell proliferation.

The term "a condition associated with undesirable cell proliferation and/or blockage of cell differentiation" is meant to encompass conditions in which abnormal cell proliferation and blockage of cell differentiation exist. Examples of such conditions include conditions involving the formation of tumours such as various cancers. The term "cancer" is used herein to refer to various cancers including, but not limited to, lymphoma, leukemia, thymoma, osteosarcoma, glyoma, intestinal cancer, lung cancer, uterine cancer, ovarian cancer, and testicular cancer.

The present method may be utilized to prevent undesirable cell proliferation in target cells in vitro as well as in vivo to treat a condition associated with undesirable cell proliferation and/or blockage of cell differentiation in a mammal. The term "mammal" is used herein to refer to both human and non-human mammals.

The term "treat" is used herein to refer to obliteration of disease, as well as amelioration thereof, including the inhibition or suppression of tumour growth, and the partial inhibition or reduction of tumour growth.

Figure 2A:
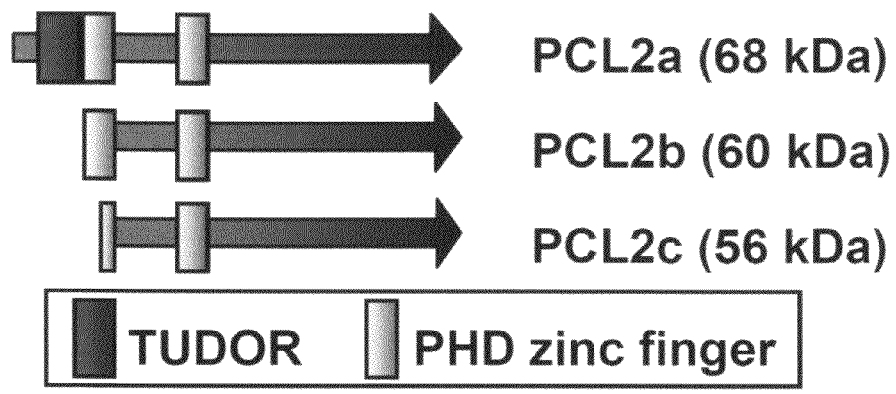
FIG. 2A is a schematic of the three isoforms of the PCL2 protein expressed in undifferentiated ESCs and the protein domains included in each.

The term "PCL2" refers to the protein product of the mammalian Pcl2 gene and is also referred to as the metal response element binding transcription factor 2 (Mtf2). As used herein, the term "PCL2" includes mammalian PCL2 as well as functionally equivalent variants thereof, for example variants of PCL2 which include 1 or more amino acid replacements particularly including conservative amino acid replacements, amino acid additions or amino acid deletions but which retain native PCL2 activity, including the ability to regulate stem cell differentiation. This can be determined using cell culturing techniques as described in more detail in the specific example herein. Examples of three isoforms of PCL2 are schematically illustrated in FIG. 2A, which include terminal modifications to PCL2. Amino acid sequences of three PCL2 isoforms are shown in FIG. 8.

Figure 7:
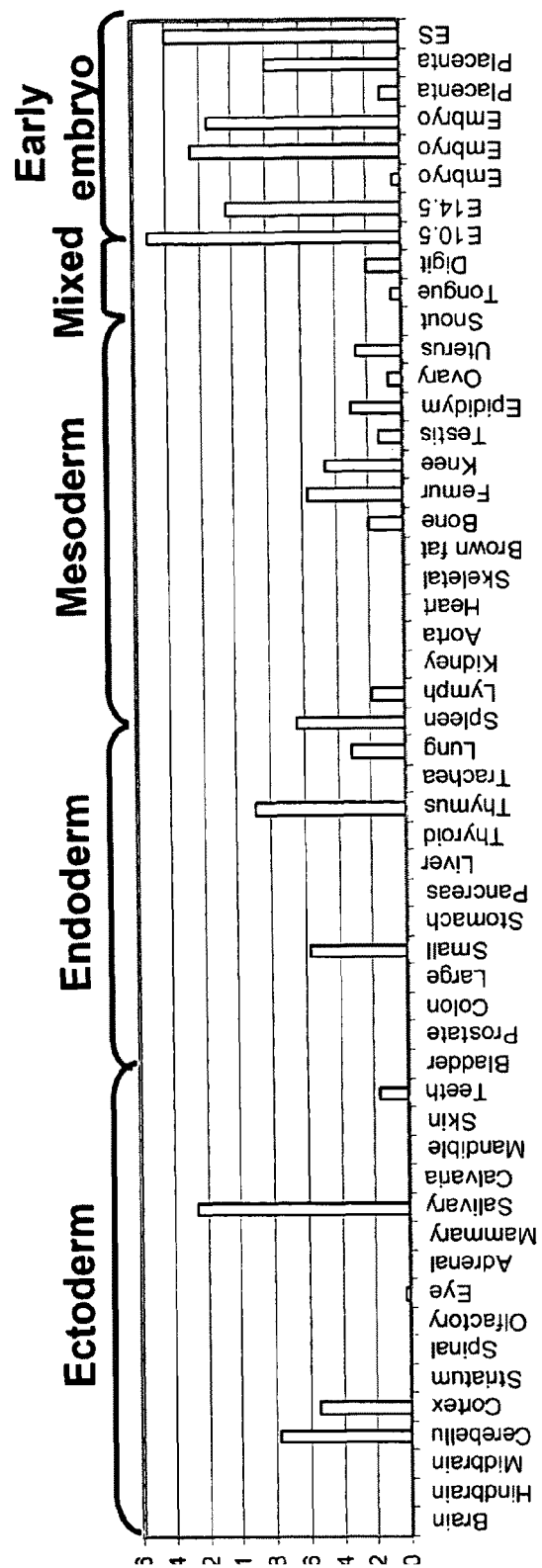
FIG. 7 is a microarray analysis on 55 tissues demonstrating that Pcl2 is expressed most highly in undifferentiated ESCs and during embryonic development, but also is highly expressed in several adult tissues (thymus, spleen, lymph, brain)

In accordance with the invention, undesirable cell proliferation, including tumour growth, may be suppressed by increasing PCL2 levels within target cells. In one embodiment, the level of PCL2 may be increased by enhanced Pcl2 gene expression to a tumour-suppressing level of Pcl2 gene expression, e.g. a level of expression that does not result in undesirable cell proliferation and blockage of cell differentiation, and preferably a normal level of expression. The term "normal" as it is used herein with respect to expression level of Pcl2, or level of PCL2 protein product, refers to levels of Pcl2 and PCL2 that generally exist in a healthy mammal, or in healthy cells or tissue. As one of skill in the art will appreciate, this level varies from tissue to tissue as shown in FIG. 7. Thus, examples of normal levels of Pcl2 expression in target tissues include the relative amounts of 0.89 for thymus, 0.63 for spleen, 0.18 for lymph, 0.78 for brain, and 1.40 for ES cell. These values represent the enhanced expression of Pcl2 in these tissues over the average expression level of Pcl2 in tissue.

Methods of gene therapy, which are well-known to those of skill in the art, may be employed to enhance Pcl2 gene expression. Generally, methods of gene therapy involve administration of functional Pcl2 gene via a vector to a target cell population, for example, in a mammal for integration into the genome to increase Pcl2 expression and thereby result in an increase of PCL2.

Alternatively, PCL2 protein may be administered directly to target cells, for example, in a mammal in need of treatment, to achieve the desired tumour-suppressing level of PCL2 within the mammal. In this regard, as indicated, a tumour-suppressing level of PCL2 will vary with the target tissue but will generally be at least an amount to achieve a normal or endogenous level of PCL2 within the target tissue.

PCL2 for this purpose may be prepared using standard, well-established solid-phase peptide synthesis methods (SPPS). Two methods of solid phase peptide synthesis include the BOC and FMOC methods. PCL2 may also be made using any one of a number of suitable techniques based on recombinant technology. It will be appreciated that such techniques are well-established by those skilled in the art, and involve the expression of the PCL2-encoding nucleic acid in a genetically engineered host cell.

Once prepared and suitably purified, PCL2 and functional variants thereof in accordance with the invention, may be utilized to treat disease. Generally, a pharmaceutical composition comprising the PCL2 protein and at least one pharmaceutically acceptable adjuvant may be used in such treatment. The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with peptide-based drugs, such as diluents, excipients and the like. Reference may be made to "Remington's Pharmaceutical. Sciences", 17th Ed., Mack Publishing Company, Easton, Pa., 1985, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tabletting agents, anti-oxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered, for example, anti-microbial agents may be added to the composition to prevent microbial growth over prolonged storage periods.

A diagnostic method is also provided herein. The level of Pcl2 expression in a biological sample from a mammal may be used to diagnose or prognose an abnormal condition in a mammal, e.g. a cancer. Thus, detection of a reduced level of Pcl2 expression in biological sample from the mammal, e.g. an amount of less than a normal amount, is indicative of a condition in which there is abnormal cell activity, e.g. increased cell proliferation and blockage of cell differentiation, that may result in a cancer, e.g. tumour formation. The term "biological sample" is used herein to include, but is not limited to, samples such as blood, urine, saliva, and tissue biopsies. Detection of reduced PCL2 levels in a tissue within a mammal, such as less than 75% of the normal expression levels of PCL2 in that tissue, preferably detection of less than 50% of the normal expression levels of PCL2 in that tissue, such as detection of less than 30-40% of the normal expression levels of PCL2 in that tissue, is also indicative of an abnormal condition in the mammal, such as a cancer.

In another aspect, a method of preparing a population of differentiated cells is provided. This method comprises the step of increasing Pcl2 expression in a population of cells, e.g. over-expressing Pcl2, in the presence of a marker which drives differentiation of the cells towards a desired cell type, such as mesoderm and ectoderm cell types including heart, liver and pancreas. This method is also useful to prepare cells for tissue engineering applications.

In another aspect of the invention, regulation of Pcl2 may be used to prepare a population of stem cells for tissue engineering applications. In this regard, a method of preparing a population of highly and homogeneously undifferentiated stem cells is provided. The method comprises the step of down-regulating or inhibiting Pcl2 expression in the stem cell population under self-renewing conditions. It may also be used to amplify an undifferentiated somatic stem cell population in vitro or in vivo. As one of skill in the art will appreciate, such down-regulation of Pcl2 expression may be achieved using well-established techniques which incorporate antisense or siRNA/shRNA technologies as described in more detail in the specific example herein.

Down-regulation of Pcl2 expression in conjunction with over-expression of induced pluripotent stem cell (iPS) genes, such as Oct4, Sox2, Klf4, c-Myc or Lin28, may also be used to reset developmental potential in the generation of iPS cells from adult cells.

In another aspect of the present invention, an article of manufacture is provided. The article of manufacture comprises packaging material and a pharmaceutical composition. The composition comprises a pharmaceutically acceptable adjuvant and a therapeutically effective amount of PCL2 protein, wherein the packaging material is labeled to indicate that the composition is useful to treat a disease associated with abnormal cell differentiation, including for example, cancer. The packaging material may be any suitable material generally used to package pharmaceutical agents including, for example, glass, plastic, foil and cardboard.

Embodiments of the invention are described by reference to the following specific example which is not to be construed as limiting.

EXAMPLE

Materials and Methods

ES Cell Culture

R1 ESCs and Oct4::eGFP ESCs (Viswanathan et al., 2003. *Supplementation-Dependent Differences in the Rates of Embryonic Stem Cell Self-Renewal, Differentiations and Apoptosis*", Biotechnol. Bioeng. 84, 505-517, the relevant contents of which are incorporated herein by reference) were cultured at 37° C. and 5% $CO_2$, on a layer of mitomycin-treated embryonic fibroblasts (MEFs) in ESC media consisting of Dulbecco modified eagle serum (DMEM) supplemented with 15% FBS (North Bio, Lot SF30408), 0.1 mM nonessential amino acids, 1 mM sodium pyruvate, 2 mM L-glutamine (all from Gibco), 1000 U/mL leukemia inhibitory factor (LIF) (ESGRO, from Chemicon, batch 11061065) and 100 µM β-mercaptoethanol (Sigma). Differentiation media formulation is described with the specific differentiation protocols listed below. Selection media consisted of ESC media supplemented with 150 µg/mL G418 (Gibco). ESCs were passaged every two days at a ratio of 1:5 by washing with PBS (Gibco), dissociating with 0.05% trypsin (Gibco) for 5 minutes at 37° C. and resuspending in ESC media. Media was changed daily.

Time Course of OCT4::eGFP ESC Differentiation

Oct4::eGFP ES cells were plated at a density allowing growth for a set number of days without overcrowding. Cells were plated on 10-cm tissue culture treated dishes (Falcon) coated with 0.1% gelatin in LIF-negative differentiation media at a density of $5 \times 10^5$ cells/dish for 5 days, $1 \times 10^6$ cells/dish for 3 days, $2 \times 10^6$ cells/dish for 2 days, or $3.5 \times 10^6$ cells/dish for 1 day of differentiation. Differentiation media was changed each day. Control, undifferentiated cells were harvested two days after plating in +LIF conditions. For FACS sorting of differentiating cells, Oct4::eGFP ES cells were trypsinized, and resuspended in 2% FBS in PBS at a dilution of $8 \times 10^6$ cells/mL. Cells were sorted into three populations based on relative GFP expression (high, medium and low). Sorted cell populations were collected, and RNA was extracted using Trizol (Invitrogen).

Time Course Microarray Hybridizations

Total RNA extracted from FACS sorted cells using Trizol (Invitrogen) was subjected to two cycles of standard cDNA synthesis and in vitro transcription. 500 ng of cRNA was used for the second cycle of amplification and 1 µg of purified cDNA from the second cycle was used for biotin labeling. Amplified and biotin-labeled cRNA was hybridized to each of the Affymetrix GeneChips MG_U74av2 and MG_U74bv2.

Time Course Microarray Analysis

The normalized data obtained from MAS5.0 analysis of the Affymetrix MGU74a and MGU74b chips of 16 time points were analyzed as follows: first, the Present/Absent/Marginal designations for each probe were used to isolate only probes for which at least one hybridization was measured as Present (14,000 probes). Probes in which all hybridizations were measured as marginal or absent were disregarded from this point forward. The data were centered by taking the average of all hybridizations for a given probe and dividing each expression value by that average in order to shift the data so that each value was a number between 0 and 1, and the average of expression values for a given probe was 1. The standard deviation across the 16 hybridizations of each probe was calculated and compared to the standard deviation of all probes (the latter calculated to be 0.449). Only probes with a standard deviation greater than 0.449 were considered further (2,700 probes in total). K-means clustering analysis was performed using the JAVA-based application Multiexperiment Viewer (MeV) v4.0 (TIGR).

Immunoprecipitations of PRC2 Members

Media was removed and cells grown on a 15-cm gelatin coated TCP dish were washed with ice cold PBS. Cells were scraped in 5 cm of ice-cold PBS with a cell scraper and centrifuged for 5 minutes at 700 rcf. The cell pellet was resuspended in Co-IP lysis buffer (150 mM NaCl, 10 mM HEPES-pH 7.5, 0.2% Igepal, 10 ug/ml protease inhibitors (aprotinin, leupeptin, pepstatin), 1 mM PMSF), incubated on ice for 30 minutes and centrifuged for 10 minutes at 2° C. The concentration was determined with the Bradford assay and 1 mg of total protein was added to 40 uL A/G sepharose-beads pre-blocked with BSA. Following a one hour incubation at 4° C., the supernatant was collected and was added to 2 ug of antibody (either PCL2 (Genway No 18-003-42503) or EZH2 (ActiveMotif No. 39103)). The protein-antibody mixture was incubated for 1-2 hours at 4° C. 40 uL of fresh A/G protein beads were added and incubated for 1 hour at 4° C. The beads were washed three times with Co-IP lysis buffer. 20 uL of loading buffer was added to the beads and boiled for 5 minutes at 99° C. Sample was separated from the beads by centrifugation and run on a 10% SDS-PAGE and the presence of EZH2, PCL2 and SUZ12 (Upstate No 04-046) was visualized using Western Blot analysis.

shRNA Vector Design

Qiagen (http://www1.qiagen.com/Products/GeneSilencing/CustomSiRna/SiRnaDesigner.aspx), Dharmacon (http://www.dharmacon.com/sidesdesign/default.aspx?source=0) and Ambion (http://www.ambion.com/techlib/misc/siRNA_finder.html) websites were used to generate a 21-base pair siRNA sequence specific to the Pcl2 mRNA sequence. Criteria for selection of an appropriate Pcl2 siRNA sequence were as follows: at least 100 nucleotides away from both the start and the termination codon, having approximately 50% GC content, having no more than three successive G or Cs or four successive A or Ts, and not homologous to any other murine gene, as determined by a BLAST search. Custom complementary oligonucleotides were synthesized (Invitrogen). Pcl2 target sequence: AAG AGC ACT CCA GAC TCA GAA (SEQ ID No. 1) and Pcl2 mismatch sequence: AAT TAC ACT CGT CAC TCA GAA (SEQ ID No. 2).

Construction of Pcl2 shRNA Transgene

Pcl2 siRNA was subcloned into a selectable plasmid shRNA vector as described in Kunath et al. (2003). Nat Biotechnol 21, 559-561, the relevant contents of which are incorporated herein by reference. The selectable plasmid shRNA vector utilizes the human H1 RNA polymerase III promoter to drive expression of the inserted siRNA sequence, and contains the neomycin-resistance gene under the control of the SV40 early promoter, enabling selection of transfected cells. 10 µL of each of the Pcl2 siRNA sense and antisense strands were combined, heated for 3 minutes at 99° C. and allowed to cool slowly to room temperature over one hour. The vector backbone was digested using Xba1 (New England Biolabs (NEB) R0145S) and Asp718 (Roche 814253), and the digested vector was isolated using the QIAquick® gel extraction kit (Qiagen). The annealed oligonucleotides were ligated into the Xba1/Asp718 digested vector using the Quick T4 DNA Ligase kit (NEB). DH5α bacteria (Invitrogen) were transformed with the resulting ligation mixture. Colonies were picked and screened for the correct sequence. Qiaprep® Miniprep kits (Qiagen) were using to extract plasmid DNA. Sequencing was performed using the BigDye sequencing kit and T7 primer. Plasmids with verified sequences were propagated and isolated using HiSpeed™ Plasmid Purification Maxi kits (Qiagen). The plasmids were precipitated with ethanol and purified with phenol chloroform (Invitrogen) to obtain a high concentration of pure plasmid for electroporation.

ESC Electroporation and Knockdown Clone Selection

25 µL of 1 µg/µL plasmid DNA, linearized with Sca1 enzyme (NEB R0122L), was added to $15 \times 10^6$ cells in one electroporation cuvette (VWR Scientific, 47727-644). Cells were electroporated with 250 V using the GenePulser XCell® (Biorad). Cells were put on ice for 10 minutes, into warmed media for 20 minutes, and plated onto two 0.1% gelatin coated 10-cm TCP dishes. Selection media was added 24 hours after electroporation and was changed daily. After seven days, 48 single colonies were picked into a V-bottom plate (Costar 3894, Corning) with 50 µL of trypsin. Colonies were trypsized and replated onto a flat-bottom 96-well plate (Falcon 35-3072) with MEFs. Colonies were maintained by splitting 1:3 onto MEFs in selection media. Clones were frozen in 2x freezing media and RNA was isolated from clones using the RNeasy® 96 kit (Qiagen) for qPCR to determine the extent of knockdown of each clone.

Protein Quantification Using Western Blot Analysis

Pcl2 mismatch control clones and Pcl2 shRNA clones were plated on 10-cm TCP dishes coated with 0.1% gelatin in −LIF differentiation media at a density of $0.5 \times 10^6$ cells/dish for 5 days of differentiation, $10^6$ cells/dish for 3 days of differentiation, $2 \times 10^6$ cells/dish for 2 days of differentiation or $3.5 \times 10^6$ cells/dish for 1 day of differentiation. Day 0 cells were harvested two days after plating in +LIF media. Cells were lysed with 1× NP40 lysis buffer including 1× protease inhibitor cocktail (Roche). Total protein concentration of each cell lysis mixture was determined using the Bradford Reagent (Sigma Aldrich). 15 µg of total protein was loaded into each lane and run through 4-15% SDS-PAGE. Western blots were probed with murine anti-OCT4 antibody (BD Transduction Laboratories), anti-3me-H3K27 antibody (Millipore 07-449) and anti-EZH2 antibody (ActiveMotif No. 39103). All antibody solutions were prepared in 5% skim milk TBST solutions. Western blot analysis was conducted with the ECL Plus Western Blotting Reagents (GE Healthcare).

Protein Quantification in Single Cells Following Removal of LIF and/or BMP4

Cells were plated in a 96-well plate (6005182; Packard) coated with a fibronectin/gelatin mixture (12.5 ug/ml fibronectin; F1141; Sigma-Aldrich, 0.02% gelatin) at a density of 12,000 cells/well for the 3-hour time-point and 6,000 cells/well for the 24-hour and 72-hour time-points. For serum replacement experiments, cells were cultured in DMEM with 15% knockout-serum replacement (10828-028; Invitrogen) in both −LIF and +LIF (ESGRO, Chemicon; ESG1106) conditions. For serum-free experiments, cells were cultured in N2B27 media with either +LIF/+BMP4, +LIF/−BMP4, −LIF/+BMP4 or −LIF/−BMP4. All cells were plated in +LIF, serum-containing media and changed to their respective media conditions after 3 hours. Each cell line was plated in triplicate. At each time-point, cells were fixed in 3.7% formalin for 10 minutes at 37° C., permeabilized with 100% methanol for 2 minutes at room temperature and stained with a primary antibody targeting Oct3 (OCT4) (611202; BD Transduction Laboratories) or me3-H3K27 (Millipore 07-449) followed by a secondary antibody AlexaFluor 546, (A-11030; Molecular Probes) and Hoechst (862096; Sigma-Aldrich) (0.1 ug/mL). Cells were imaged using the ArrayScan II automated fluorescent microscope (Cellomics). Average pixel intensity of Primary Ab:AlexaFluor 546 fluorophore within the nuclear area (as defined by Hoechst staining) of individual cells was determined. 10,000 individual cells were imaged and the percentage of positive and negative cells was determined.

Quantitative Real-Time PCR

Total RNA was isolated using RNeasy Mini kit (Qiagen) and then treated with DNase (DNAfree kit, Ambion). RNA (1 µg) was reverse transcribed using Super-Script II RNase H Reverse Transcriptase (Invitrogen) with oligo(dT)23 primers (Sigma). Mouse genomic DNA standards or the cDNA equivalent to 10 ng of total RNA were added to the qPCR reaction in a final volume of 10 µL containing: 1× PCR buffer (without $MgCl_2$), 3 mM $MgCl_2$, 0.2 mM dNTP, SYBR Green I (Molecular Probes) and 0.5 µM primers. Amplification conditions were: 95° C. (3 min); 40 cycles of 95° C. (10 s), 65° C. (15 s), 72° C. (20 s); 95° C. (15 s), 60° C. (15 s), 95° C. (15 s). qPCR was performed using the Roche Light Cycler 480. Primers were designed using Primer3 and synthesized by Invitrogen. Serial dilutions of mouse genomic DNA at concentrations of 9 ng, 3 ng, 1 ng, 0.3 ng and 0.1 ng were run on each plated with each primer as described in Yuan et al. (1995). Genes & development 9, 2635-2645, the relevant contents of which are incorporated herein by reference. Housekeeping gene Elongation factor 1 was run on each plate. Measured transcript levels were normalized to the housekeeping genes and compared to a control, untreated sample. Samples were run in triplicate. Primer sequences:

```
Pcl2 F: AGGGAATTGCACATTCATCC,           (SEQ ID No. 1)
Pcl2 R: CACAATGCCTGGAAATGCTA,           (SEQ ID No. 2)

Oct4 F: CCCGAAGCCCTCCCTACA,             (SEQ ID No. 3)
Oct4 R: TCCTTCTCTAGCCCAAGCTGAT,         (SEQ ID No. 4)

Sox 2F: GCGTCAAGAGGCCCATGA,             (SEQ ID No. 5)
Sox 2R: CTGATCTCCGAGTTGTGCATCT,         (SEQ ID No. 6)

Tcl1 F: GTCCTGCAGCTCCTGTCTG,            (SEQ ID No. 7)
Tcl1 R: CTTGGAGCCCAGTGTAGAGG,           (SEQ ID No. 8)

Klf4 F: CCAAAGAGGGGAAGAAGGTC,           (SEQ ID No. 9)
Klf4 R: CTGTGTGAGTTCGCAGGTGT,           (SEQ ID No. 10)

Ezh2 F: GCTGCTGCTCTTACTGCTGA,           (SEQ ID No. 11)
Ezh2 R: CCAGTTTCAGTCCCTGCTTC,           (SEQ ID No. 12)

Fgf5 F: ACTGAAAAGACAGGCCGAGA,           (SEQ ID No. 13)
Fgf5 R: TGAACCTGGGTAGGAAGTGG,           (SEQ ID No. 14)

Gsc F: AAAGCCTCGCCGGAGAA,               (SEQ ID No. 15)
Gsc R: AGCTGTCCGAGTCCAAATCG,            (SEQ ID No. 16)

Lhx1 F: CACCTCAACTGCTTCACCTG,           (SEQ ID No. 17)
Lhx1 R: TGTTCTCTTTGGCGACACTG,           (SEQ ID No. 18)

T F:    TCCTCCATGTGCTGAGACTTGT,         (SEQ ID No. 19)
T R:    TGCCACTTTGAGCCTAGAAGATC,        (SEQ ID No. 20)

Wnt3 F: CAGCGTAGCAGAAGGTGTGA,           (SEQ ID No. 21)
Wnt3 R: GCCAGGCTGTCATCTATGGT),          (SEQ ID No. 22)

Bmi1 F: AGAAGAAATGGCCCACTACCTTT,        (SEQ ID No. 23)
Bmi1 R: CCCTCTGGTGACTCATCTTCATTC,       (SEQ ID No. 24)

Fgf8 F: CACAGAGATCGTGCTGGAGA,           (SEQ ID No. 25)
Fgf8 R: TGTACCAGCCCTCGTACTTG,           (SEQ ID No. 26)

Hand1 F: CAAACGAAAAGGCTCAGGAC,          (SEQ ID No. 27)
Hand1 R: ATGCTCTCTGTGCGTCTCCT,          (SEQ ID No. 28)

Eomes F: GTGGCGCTTATCAGAGGAAG,          (SEQ ID No. 29)
Eomes R: TTTTTCCTTGGCAAGCTGAT,          (SEQ ID No. 30)

Flk-1 F: TTCTGGACTCTCCCTGCCTA,          (SEQ ID No. 31)
Flk-1 R: GCACACTTCCTCTTCCTCCA,          (SEQ ID No. 32)

Flt1 F: TGCAGGACGATGAATCTGAG,           (SEQ ID No. 33)
Flt1 R: ATACTGTCAGGGGCTGGTTG,           (SEQ ID No. 34)

Gata6 F: GAACGTACCACCACCACCAT,          (SEQ ID No. 35)
Gata6 R: CCATGTAGGGCGAGTAGGTC,          (SEQ ID No. 36)

Gata4 F: GAGATGGGACGGGACACTAC,          (SEQ ID No. 37)
Gata4 R: TTGATGCCGTTCATCTTGTG,          (SEQ ID No. 38)

Bmp2 F: GCTCCACAAACGAGAAAAGC,           (SEQ ID No. 39)
Bmp2 R: AGCAAGGGGAAAAGGACACT,           (SEQ ID No. 40)

Hnf4 F: AGTAACCTAGTCATGGCAAAGAAGATG,    (SEQ ID No. 41)
Hnf4 R: GGGCCTCACACCCTTTCTG,            (SEQ ID No. 42)

Hoxb1 F: CATCAGCCTACGACCTCCTC,          (SEQ ID No. 43)
Hoxb1 R: GGAGTGAGAGTGCTGGGTTC,          (SEQ ID No. 44)

Nestin F:   CCCTCTGGCACTGAGGACTTAGT,    (SEQ ID No. 45)
Nestin R:   CACAGGTCAAGTTATCAAAGCTAAGAGT, (SEQ ID No. 46)

Cdx2 F: TGGAGCTGGAGAAGGAGTTT,           (SEQ ID No. 47)
Cdx2 R: CAGCCAGCTCACTTTTCCTC            (SEQ ID No. 48)
```

Colony Forming Assay and Alkaline Phosphatase Staining

Single cell suspensions of Pcl2 mismatch controls and Pcl2 shRNA clones were plated in a 12-well dish at a density of 500 cells/well. Colonies were grown in +LIF conditions for 5 days with media changed daily. The respective ESC clones were fixed in 10% cold neutral formalin buffer (NFB: 100 mL formalin, 16 g $Na_2HPO_4.H_2O$ in 1 L ddH2O) for 45 min. Alkaline phosphatase (ALP) stain was made: 0.01 g Naphthol AS MX-PO4 (N4875, Sigma) dissolved in 400 μL N,Ndimethylformamide (DMF; Sigma), 25 mL 0.2M Tris-HCl (pH=8.3), 0.06 g red violet LB salt in 25 mL ddH2O and filtered through Whatman's No. 1 filter paper. ALP stain was added to the fixed ESCs and allowed to incubate for 1h at room temperature. Stained cells were washed three times with PBS and imaged with the Leica DC200 light microscope and Leica IM50 V1.20 software. Upon imaging, ESC colonies were classified as differentiated if there was little or no ALP stain present and undifferentiated if the colony stained positive for ALP expression and had the rounded, smooth-edged morphology of undifferentiated ESCs.

Time Course of Embryoid Body Differentiation 1 million ESCs in a 10 mL suspension were added to a 10-cm uncoated tissue culture plate. Media consisting of Dulbecco modified eagle serum (DMEM) supplemented with 15% FBS, 0.1 mM nonessential amino acids, 1 mM sodium pyruvate, 2 mM L-glutamine (all from Gibco) and 100 μM β-mercaptoethanol (Sigma). After 1 day, 5 mL additional media was added to the plate. After 2 days, 1 mL of EBs were collected for RNA extraction using the Qiagen RNeasy kit. Also after 2 days, half of the suspension was added to a new plate and topped up to 10 mL with fresh media. This was continued for the duration of the time course. After 25 days in suspension, EBs were trypsinized and plated as single-cell suspension onto a gelatin-coated 10-cm TCP dish in +LIF conditions. Following 3 days, cells were fixed, stained for ALP and undifferentiated colonies were quantified.

Time Course of Neural Differentiation

Pcl2 shRNA and Pcl2 mismatch control cells were plated in N2B27 media, according to Ying et al. (2003b). Nat Biotechnol 21, 183-186, the relevant contents of which are incorporated herein by reference, on gelatin and cultured for 5 days. Media was changed every second day. Cells were fixed in 3.7% formalin for 40 minutes at room temperature, permeabilized with 100% methanol for 20 minutes at room temperature and stained with a primary antibody targeting Oct3 (OCT4) (611202; BD Transduction Laboratories) or Nestin (R&D No MAB1259) followed by a secondary antibody AlexaFluor 488, (A-11030; Molecular Probes) and Hoechst (862096; Sigma-Aldrich) (0.1 ug/mL). Cells were imaged using a fluorescent microscope (Leica DMIRE2).

Microarray Hybridizations of Pcl2 shRNA Cell Lines

Total RNA was extracted from Pcl2 mismatch controls and one Pcl2 shRNA clone with RNeasy columns (Qiagen). RNA quality was tested using an Agilent Bioanalyzer before performing standard cDNA synthesis (Invitrogen Superscript) and in vitro transcription (IVT) (Enzo IVT kit). 10 ug of RNA was used for IVT and 15 ug of cRNA was used for hybridization (EukGE-WS2v4 kit) to the Mouse Genome 430 2.0 GeneChip. Scanning was performed using the Affymetrix GeneChip Scanner 3000 and analysis done using GCOS 1.4 to obtain signal-log-ratios of the control to the sample. Hybridizations of three biological replicates for both the control and Pcl2 shRNA clone were performed.

Results

Identification of Pcl2 as a Stem Cell Fate Regulator

An Affymetrix microarray screen for regulators of ESC self-renewal and commitment was performed on R1 ESCs expressing transgenic eGFP driven by the Oct4 promoter to capture the expression profile of ESCs at the transition from self-renewal to commitment. Expression data was combined with available ChIP-chip analyses to determine novel regulatory networks controlling ESC fate. To identify these networks, two time courses of differentiation were employed. The mouse Oct4::eGFP R1 ESCs were differentiated in monolayer culture following either LIF withdrawal or LIF withdrawal supplemented by RA addition.

Cells at each time point, including undifferentiated controls, expressed variable levels of eGFP. Despite this, the vast majority of the control population showed high eGFP expression, which decreased throughout both time courses. eGFP expression decreased more rapidly in the RA time course, likely due to the direct repression of the Oct4 promoter, which contains a RA response element. At each time point, cells sorted by eGFP expression were designated as "high", "medium" and "low", while recognizing that all three populations in fact exhibited very high eGFP expression and were thus likely still at the initial stages of differentiation (i.e., commitment). All cells below the "low" threshold were discarded to avoid confounding results with gene expression changes occurring in more differentiated cells. Microarray analysis was performed on each sorted population of cells. Microarray probes targeting Oct4 showed gradual and consistent down-regulation throughout both time courses, as predicted by the down-regulation in eGFP, as did Nanog and Sox2 probes. Oct4 down-regulation was confirmed by quantitative real-time PCR (qPCR).

Thus, by differentiating ESCs under carefully defined conditions, a model of the initial stages of commitment emerged, the validity of which was supported by the observed incremental losses in Oct4, Nanog and Sox2. Studying global gene expression changes at these time points enabled the description of temporal relationships between genes involved in pluripotency and commitment.

Figure 1A:
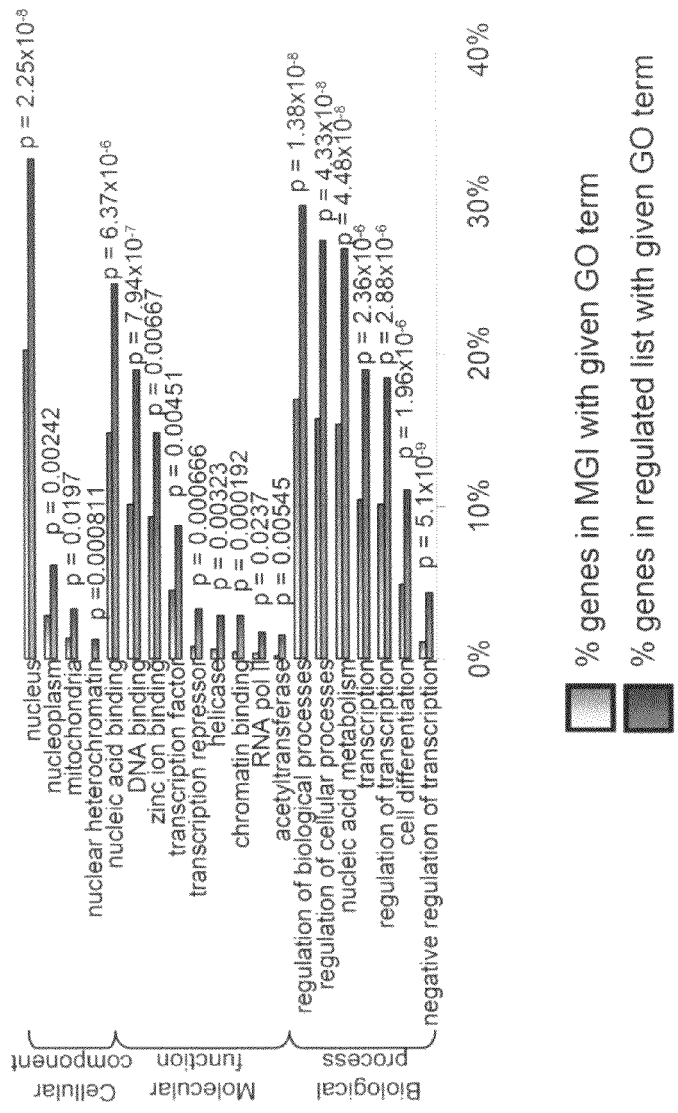
FIG. 1A illustrates the cluster of the 632 genes that were down-regulated following withdrawal of LIF from the Oct4::eGFP R1 ESCs. Clustering was performed using the K-means clustering algorithm. GO analysis was performed on this gene set and over-represented. GO terms are displayed in the bar graph.
Figure 1B:
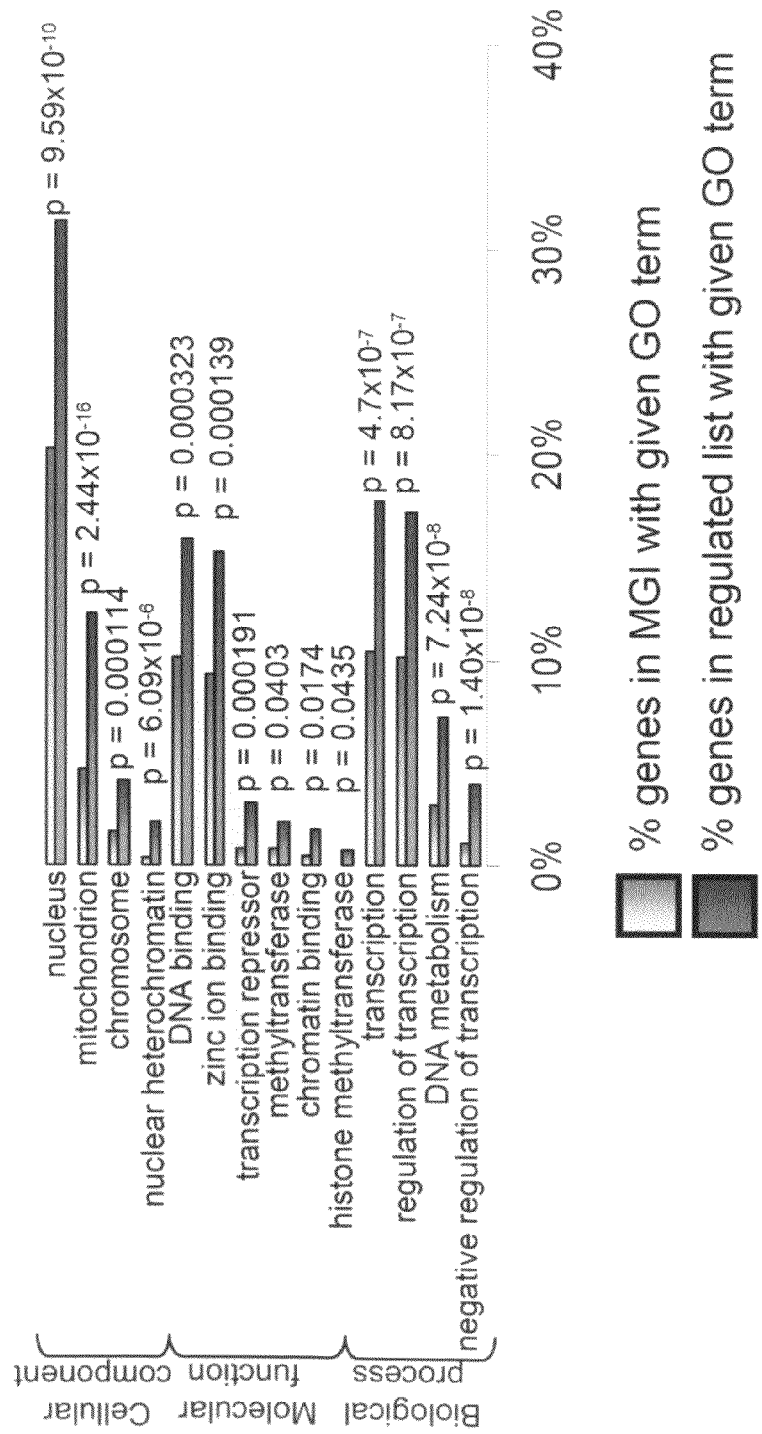
FIG. 1B illustrates the cluster of 1,206 genes that were down-regulated following withdrawal of LIF supplemented by addition of RA from the Oct4::eGFP R1 ESCs. Clustering was performed using the K-means clustering algorithm. GO analysis was performed on this gene set and over-represented GO terms are displayed in the bar graph.
Figure 1C:
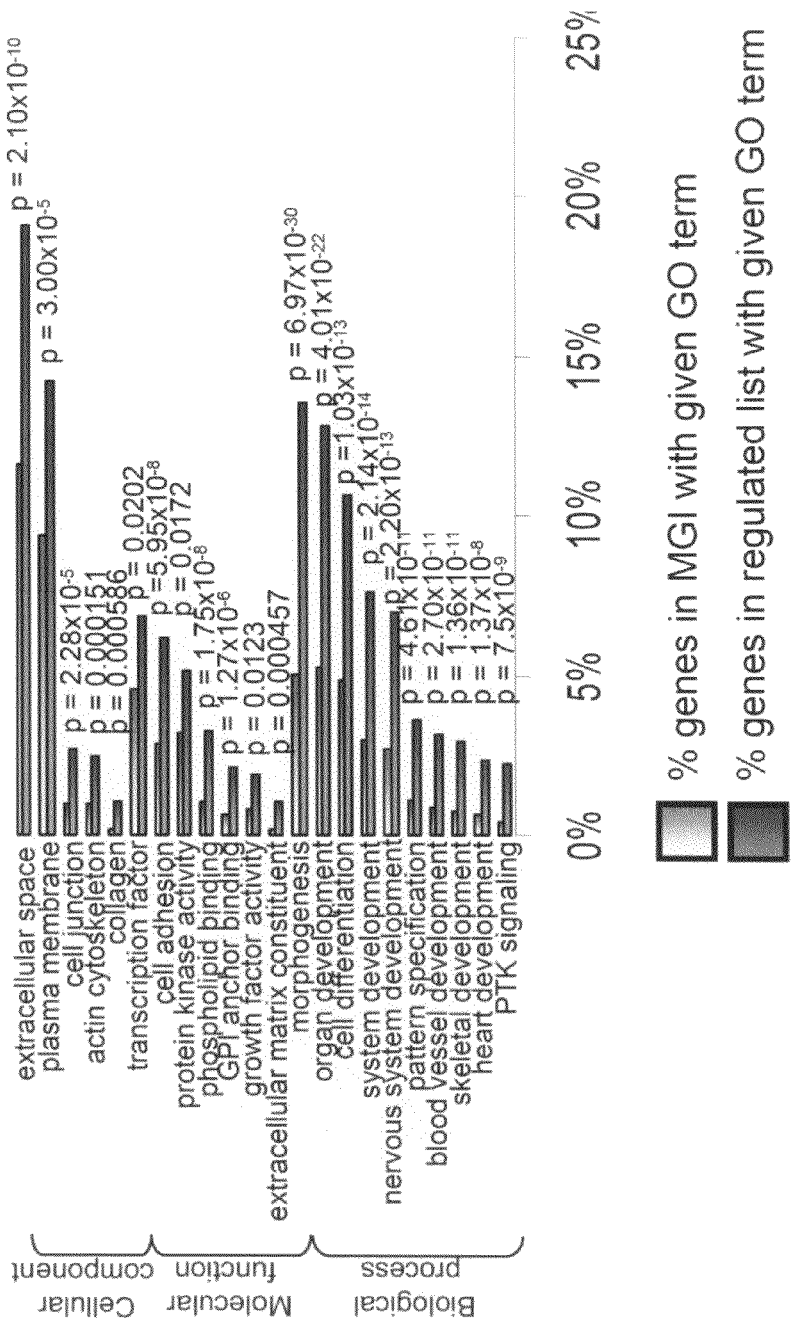
FIG. 1C illustrates the cluster of 1,379 genes that were up-regulated following withdrawal of LIF from the Oct4::eGFP R1 ESCs. Clustering was performed using the K-means clustering algorithm. GO analysis was performed on this gene set and over-represented GO terms are displayed in the bar graph.
Figure 1D:
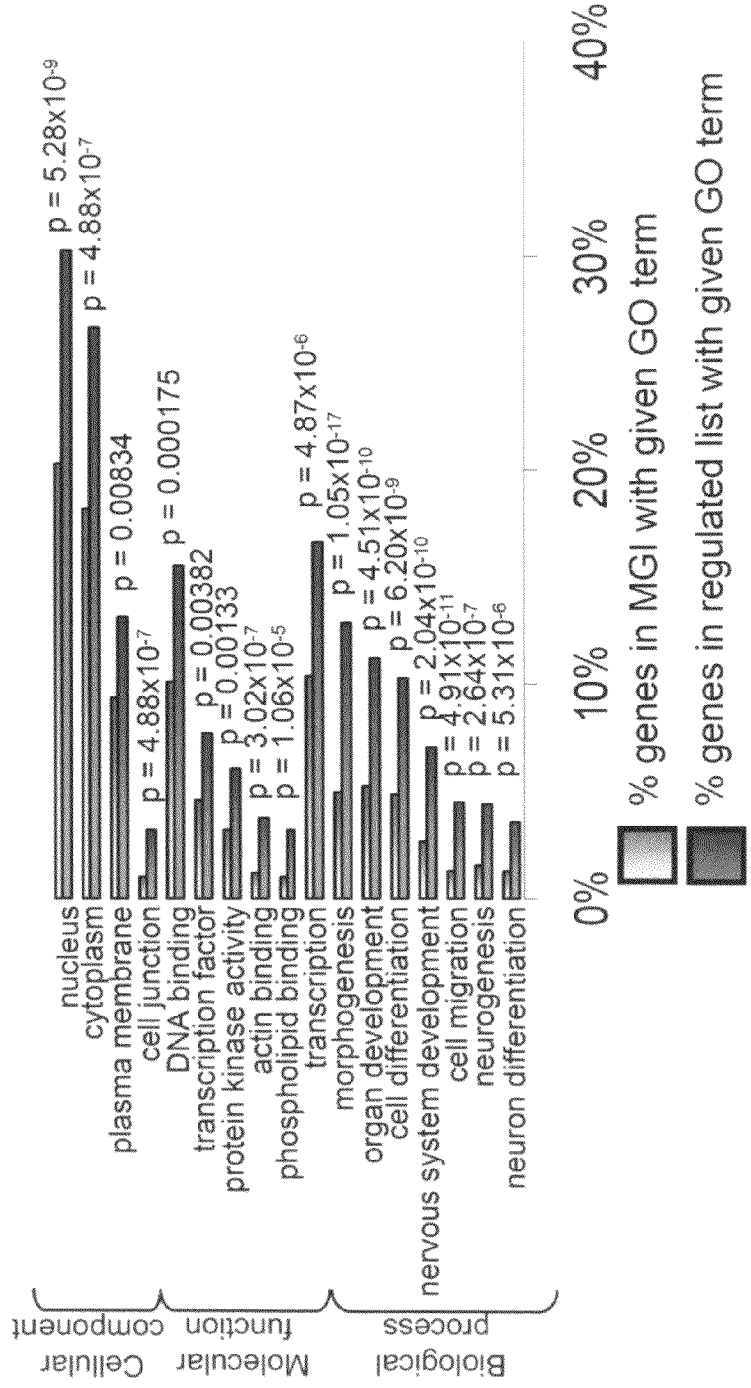
FIG. 1D illustrates the cluster of 1,351 genes that were down-regulated following withdrawal of LIF supplemented by addition of RA from the Oct4::eGFP R1 ESCs. Clustering was performed using the K-means clustering algorithm. GO analysis was performed on this gene set and over-represented GO terms are displayed in the bar graph.

Analysis of the two time courses was performed separately to obtain four lists: down or up-regulated following either LIF withdrawal or RA addition (FIG. 1A-D). A list of Gene Ontology (GO) terms that showed statistically significant overrepresentation within each regulated group, compared to the representation of that GO term within the list of mouse genes in the MGI database, described in Beissbarth et al. 2004. Bioinformatics (Oxford, England) 20, 1464-1465, incorporated herein by reference was prepared. Down-regulated lists, which included Pcl2, were enriched for transcription factors, transcriptional repressors, DNA binding proteins and chromatin remodeling genes (FIGS. 1A and 1B). Up-regulated genes were involved in transcription, but also with cell differentiation, morphogenesis, pattern specification and tissue, organ and system development (FIGS. 1C and 1D).

Only those genes exhibiting tight correlation between sorted cell populations were selected and a temporal cascade of genes regulated during early commitment was created by sorting according to the first day upon which they showed altered expression. It was found that 74% of the genes down-regulated following LIF withdrawal were also down-regulated following RA addition. These genes include Oct4, Nanog and Sox2, previously identified targets of OCT4-Fgf4, Utf1, Fbxo15, Rex1 (Zfp42) and Foxd3 transcriptional repressors, histone acetyltransferases, DNA and histone methyltransferases and PcG genes Eed, Phc1 and Pcl2. No association between Pcl2 and stem cell self-renewal and commitment has been previously established.

Figure 2B:
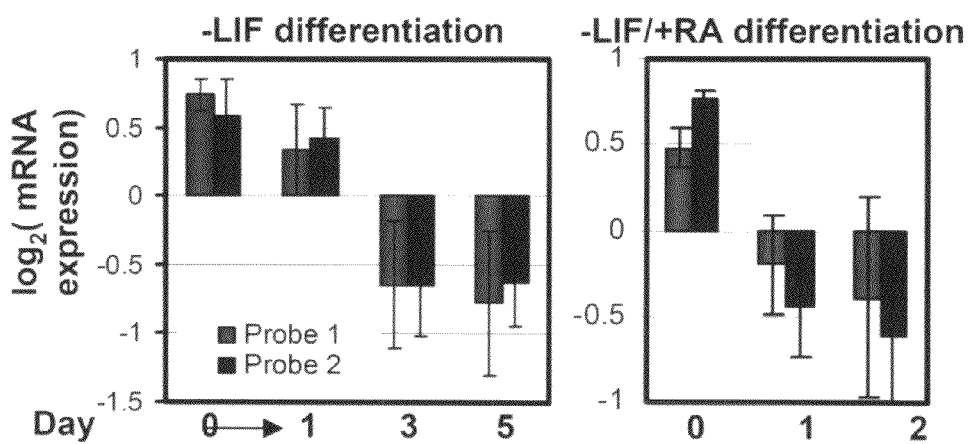
FIG. 2B illustrates the expression profile of Pcl2 in ES cells cultured in the absence (−) of LIF for 0, 1, 3 or 5 days, or in the presence (+) of RA for 0, 1 or 2 days, as determined by microarray analysis.
Figure 2C:
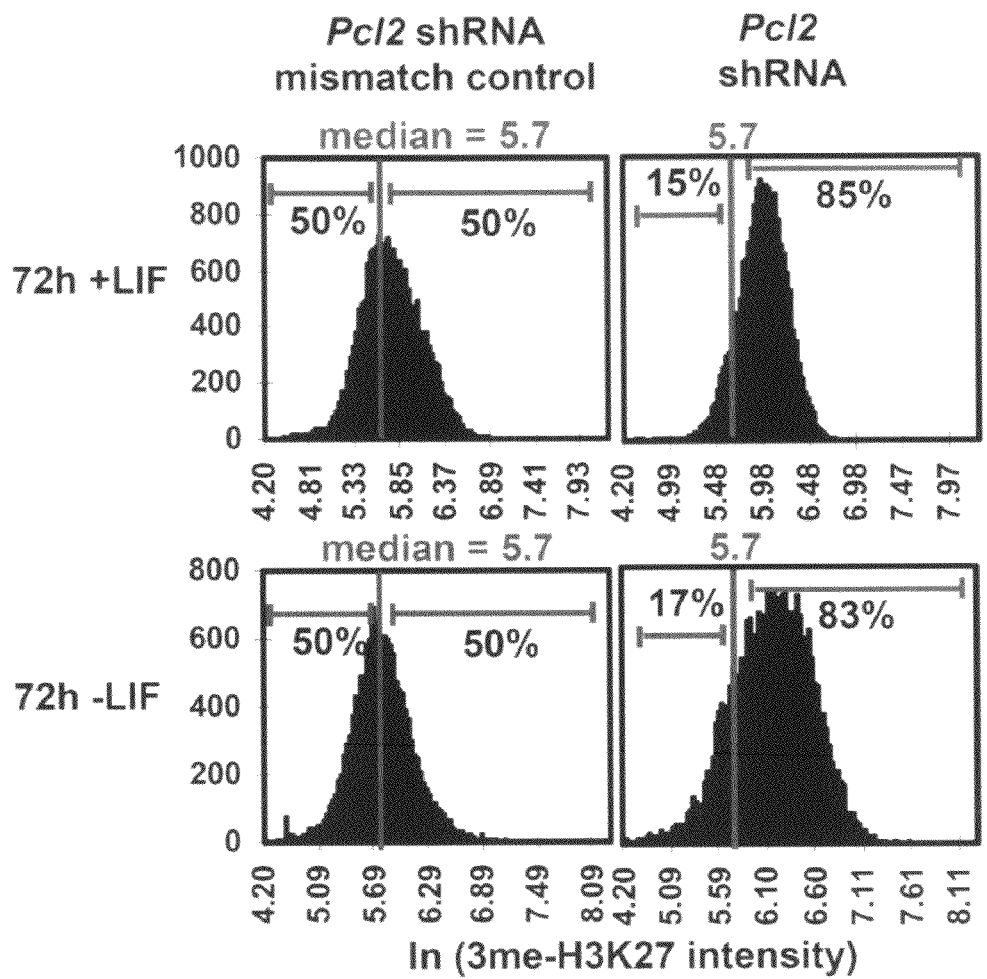
FIG. 2C illustrates a histogram of 3me-H3K27 levels in Pcl2 shRNA cells in the presence and absence of LIF over a 72 hour period demonstrating that down-regulation of Pcl2 expression leads to an increase in 3me-H3K27 levels. Data represents 3me-H3K27 in 10,000 individual cells.

Pcl2 was down-regulated following both LIF withdrawal and RA addition FIG. 2B. The kinetics of Pcl2 repression was comparable to the kinetics of the known ESC regulators. Oct4, Sox2 and Nanog. The kinetics of PCL2 protein down-regulation in R1 cells was also comparable to OCT4 protein down-regulation.

Next, ChIP-chip data sets describing promoter occupancy by OCT4, NANOG and SOX2 were incorporated. Genes identified by either group were considered as valid potential targets. The following were bound by some combination of OCT4, NANOG and SOX2: 1) 20% of genes down-regulated following LIF withdrawal; 2) 23% of genes down-regulated following RA addition; 3) 34% of genes common to both time courses; 4) 28% of the genes up-regulated following LIF withdrawal; 5) 29% of genes up-regulated following RA addition; and 6) only 7.2% of the unregulated control group. Thus, the screen, designed to identify key pluripotency genes, also systematically enriched for genes bound by, and thus potentially regulated by OCT4, SOX2 and NANOG. The promoter of Pcl2 was bound by both OCT4 and NANOG, indicating that its expression is controlled by two master regulators of self-renewal and pluripotency.

Identification of PCL2 as a Component of the PRC2 Complex

Studies in *Xenopus* and *Gallus gallus* both illustrate that the respective PCL2 homologues associate with the PRC2 complex through interaction with EZH2. Co-immunoprecipitation analyses were performed to evaluate interaction between PCL2 and both EZH2 and SUZ12, two of the core components of the PRC2 complex in mouse. Lysates were extracted from R1 ES cells and co-immunoprecipitation was determined following incubation of lysates with one of anti-PCL2, anti-EZH2 or anti-SUZ12 antibodies. Immunoprecipitates were subjected to polyacrylamide gel electrophoresis and Western blot analysis using anti-PCL2, anti-EZH2 and anti-SUZ12 antibodies. The data showed that PCL2 co-immunoprecipitated with both EZH2 and SUZ12. Similarly, EZH2 co-immunoprecipitated with PCL2. This indicates that PCL2 is a component of the PRC2 complex in undifferentiated mouse ES cells.

Down-Regulation of Pcl2 Leads to Altered Abundance of PRC2 Complex Members and 3me-H3K27

To further explore the function of Pcl2 in ESCs, and in particular its capacity to alter the state of PRC2 and corresponding histone methylation patterns, endogenous Pcl2 expression was down regulated ("knocked down") using short hairpin RNA (shRNA). Pcl2 expression was silenced through the generation of stably transfected shRNA knockdown ESC lines using a plasmid vector having an H1 pol III promoter driving expression of hairpin loop Pcl2 shRNA. The SV40 early promoter drove expression of the neomycin-resistance gene permitting selection of neomycin-resistant clones. Three siRNA sequences targeting different regions of the Pcl2 mRNA were used to eliminate the possibility of off-target effects. Corresponding mismatch control sequences in which 5 of the 21 bases of the siRNA sequence were altered were also used to generate stable control cell lines. In all shRNA experiments, results using Pcl2 shRNA knockdown cell lines are compared to the corresponding mismatch control cell line.

Figure 3A:
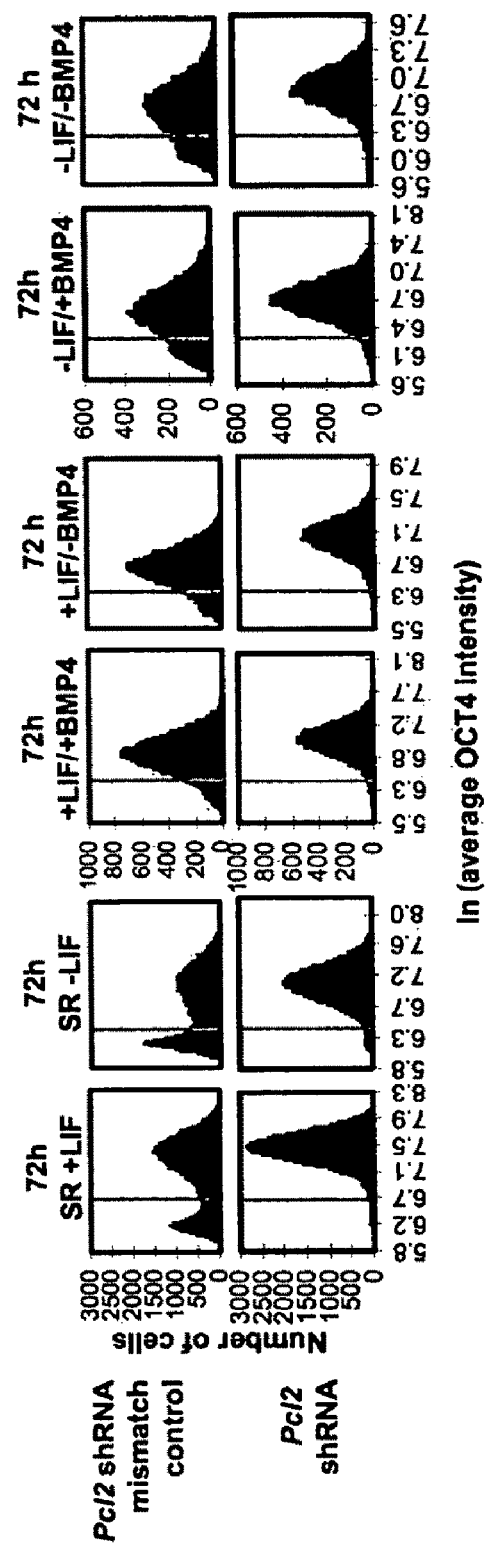
FIG. 3A illustrates histograms of OCT4 protein expression levels in Pcl2 shRNA cells in the presence and absence of LIF and in the presence and absence of BMP4 over a 72 hour period demonstrating that down-regulation of Pcl2 expression leads to an increase of OCT4 protein levels maintains the undifferentiated phenotype. Data represents OCT4 protein expression in 10,000 individual cells.
Figure 3B:
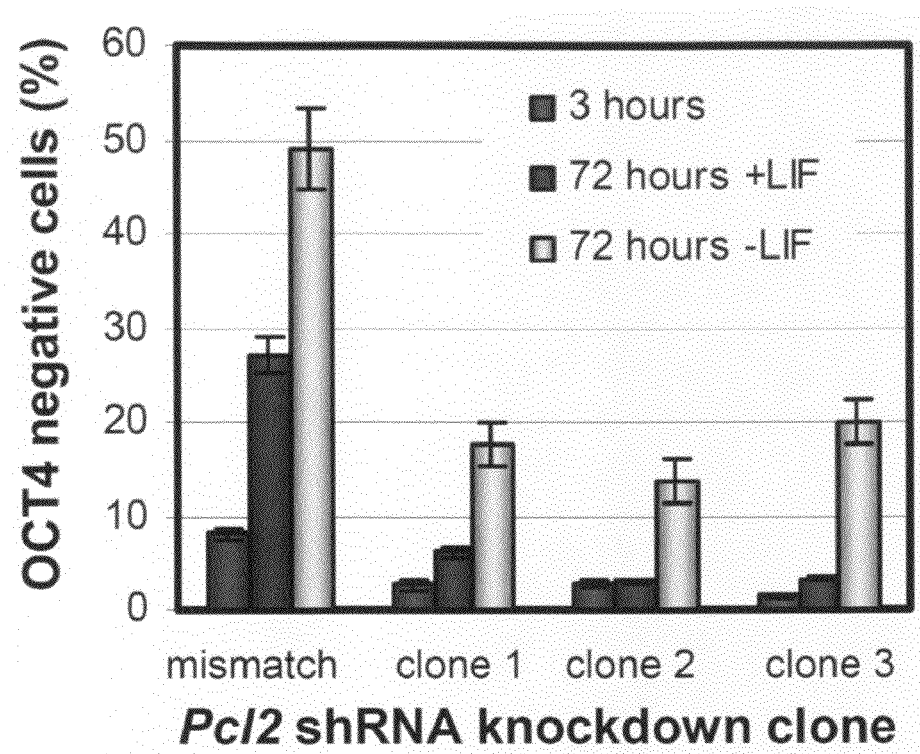
FIG. 3B quantifies the percentage of OCT4 negative cells in Pcl2 shRNA cells in the presence and absence of LIF over a 72 hour period.
Figure 3C:
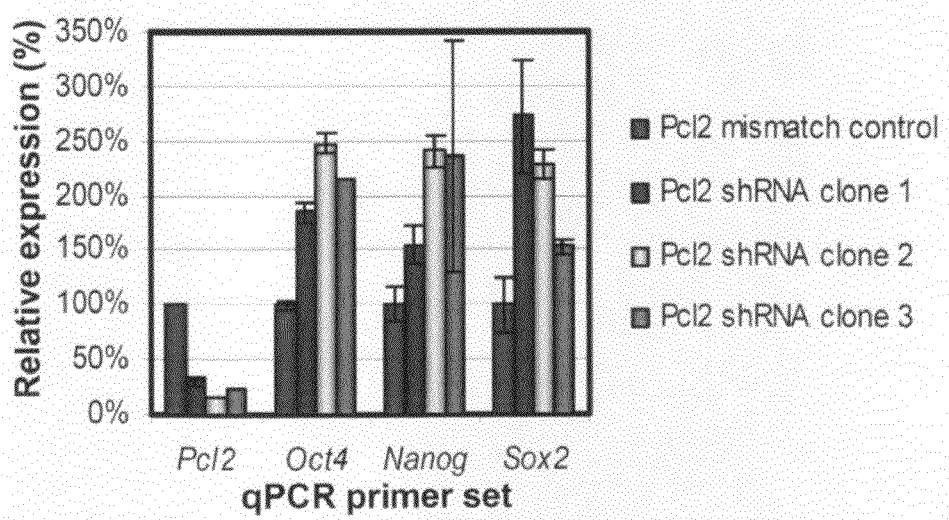
FIG. 3C is quantitative real-time PCR data representing increased Oct4, Nanog and Sox2 mRNA levels following Pcl2 knockdown in three individual Pcl2 shRNA clones.
Figure 3D:
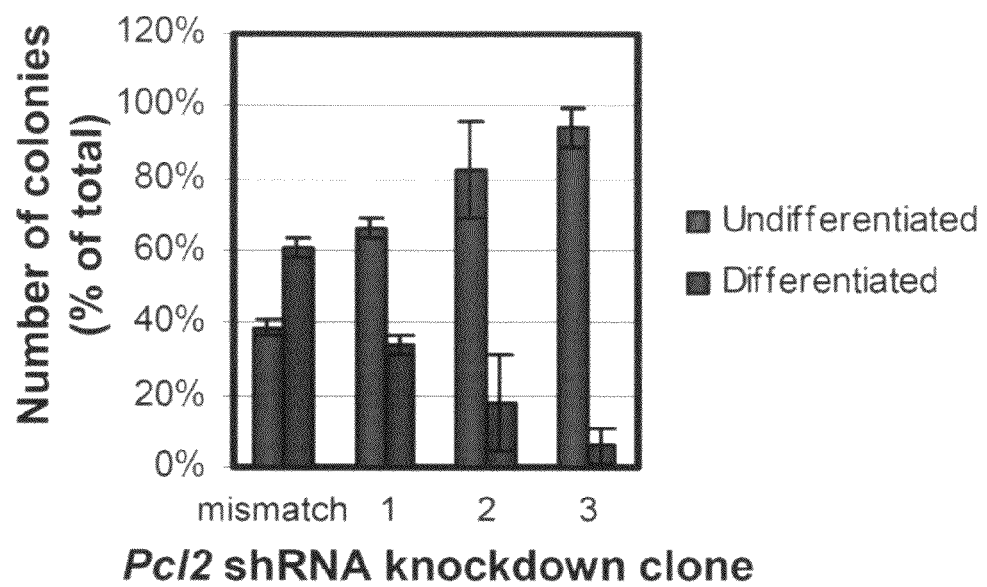
FIG. 3D represents the percentage of total alkaline phosphatase stained ES cell colonies characterized as differentiated or undifferentiated following stable transfection with Pcl2 shRNA or a control mismatch shRNA sequence.

Quantitative RT-PCR was performed on twenty-four Pcl2 knockdown ES cell clones and twelve mismatch control ES cell clones using two unique primer sequences specific to Pcl2. Three Pcl2 knockdown clones were chosen which exhibited at least 70% reduction in mRNA, compared to the mismatch control (FIG. 3C). These three clones were used in all subsequent experiments. For figures in which the results of only one clone are depicted, corresponding results were also observed for both other clones. Knockdown of Pcl2 also resulted in decreased PCL2 protein levels as assayed by Western blot analysis and immunostaining (FIG. 3D).

To determine the effect of Pcl2 reduction on PRC2 members during early differentiation, protein was extracted at days 0, 1, 3 and 5 of monolayer differentiation following the withdrawal of LIF. Protein samples were subjected to polyacrylamide gel electrophoresis and western blot analysis using anti- PCL2, anti-EZH2 and anti-SUZ12 antibodies. Reduction of PCL2 protein corresponded with an increased abundance of EZH2 proteins. Since PRC2 is responsible for depositing the repressive mark 3me-H3K27, the Western blot was stained with an antibody specific to this histone modification. In agreement with the over abundance of EZH2, the methyltransferase responsible for these modifications, 3me-H3K27 was dramatically up-regulated in day 0 and day 1 of the Pcl2 shRNA differentiation time course, as compared to control. Levels of this modification appear to return to normal by day 5 of differentiation.

To further quantify the alterations in histone modifications, high content imaging analysis of Pcl2 shRNA and control cells cultured for 72 hours in both the presence and absence of LIF was performed. The cells were stained with primary antibody 3me-H3K27 followed by AlexaFluor 488 secondary antibody and the resulting fluorescence was quantified for 10,000 individual cells in triplicate. This analysis revealed that after 72 hours in both + and −LIF, 85% of Pcl2 shRNA cells express 3me-H3K27 at a level higher than the median 3me-H3K27 expression of the control (FIG. 3C):

These data reveal that reduced Pcl2 expression leads to over-abundance of the other PRC2 complex members EZH2 and as a result leads to an increase in 3me-H3K27, a repressive histone modification controlled by the PRC2 complex and specifically mediated by the histone methyltransferase EZH2.

Down-Regulation of Pcl2 Leads to Enhanced Self-Renewal in ES Cells

To explore the effect of Pcl2 shRNA on the phenotype of the undifferentiated ESC, a self-renewal assay using single cell, high content imaging analysis was employed. The assay uses immunofluorescence imaging to quantitatively measure OCT4 protein expression at a single cell level as a surrogate marker of ESC self-renewal. Loss of OCT4 protein expression and, thus, decrease of fluorescence below a calculated threshold, signified cell differentiation. Pcl2 shRNA and control cells were cultured under multiple differentiative conditions to study the effects of known self-renewal mediators LIF and BMP4. Specifically, cells were cultured in: 1) serum replacement media +LIF; 2) serum replacement media −LIF; 3) serum-free media +LIF/+BMP4; 4) serum-free media +LIF/−BMP4; 5) serum-free media −LIF/+BMP4 and 6) serum-free media −LIF/−BMP4. In all cases, Pcl2 shRNA clones were able to maintain higher levels of OCT4 protein, even in −LIF conditions (FIG. 4A and 4B). In serum-replacement conditions, control cells develop an OCT4 negative population of cells in −LIF, however, no such population emerged in the Pcl2 shRNA clones. In the absence of both LIF and BMP4, the survival of both controls and Pcl2 shRNA clones was reduced, however, the surviving Pcl2 shRNA cells continued to express high levels of OCT4 (FIG. 4A).

qPCR was performed to measure the mRNA levels of Oct4 as well as additional self-renewal markers Sox2 and Nanog. In all three Pcl2 shRNA clones tested, levels of these three markers were increased by approximately 200% (FIG. 4C). This data is supported by Western blot analysis showing that OCT4 protein is elevated in Pcl2 shRNA clones in +LIF as well as day 1 and day 3 of −LIF differentiation (FIG. 3C).

Figure 5:
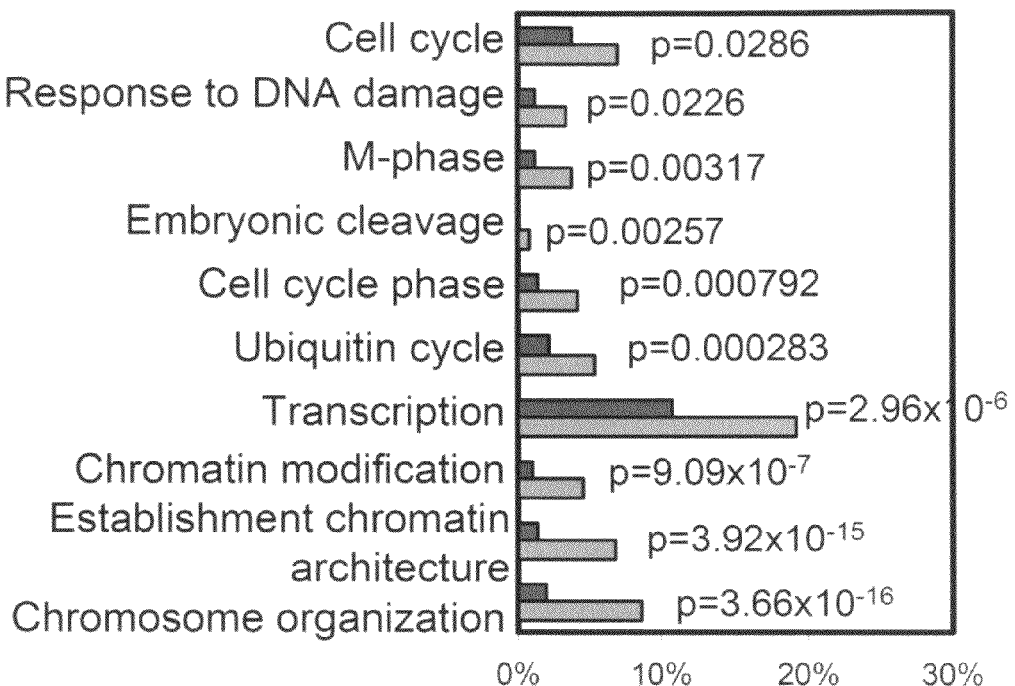
FIG. 5A is microarray data showing that gene ontology (GO) terms over-represented amongst genes up-regulated in the Pcl2 shRNA cells are involved in cell cycle, transcription and chromatin remodeling.
FIG. 5B shows that GO terms over-represented amongst down-regulated genes are involved in development.
FIG. 5C shows that markers of undifferentiated ESCs are up-regulated and markers of mesoderm are dramatically down-regulated in Pcl2 shRNA clones.
FIG. 5D shows that expression of positive regulators of cell cycle and oncogenes are up-regulated, tumour suppressors and negative regulators of cell cycle are down-regulated in Pcl2 shRNA clones.
Figure 5:
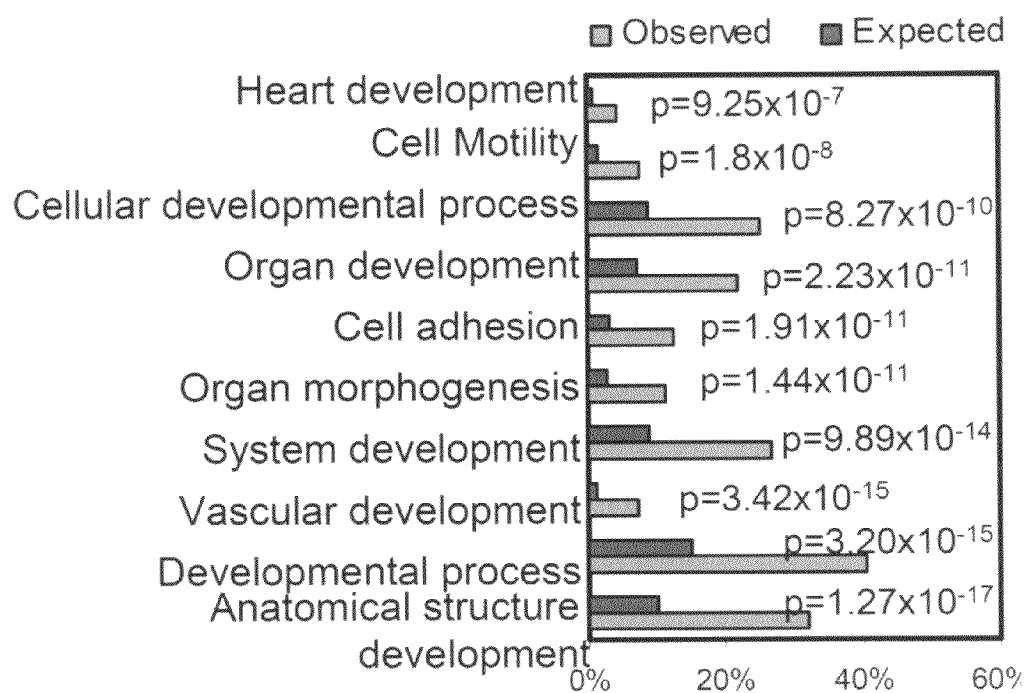
Figure 5C:
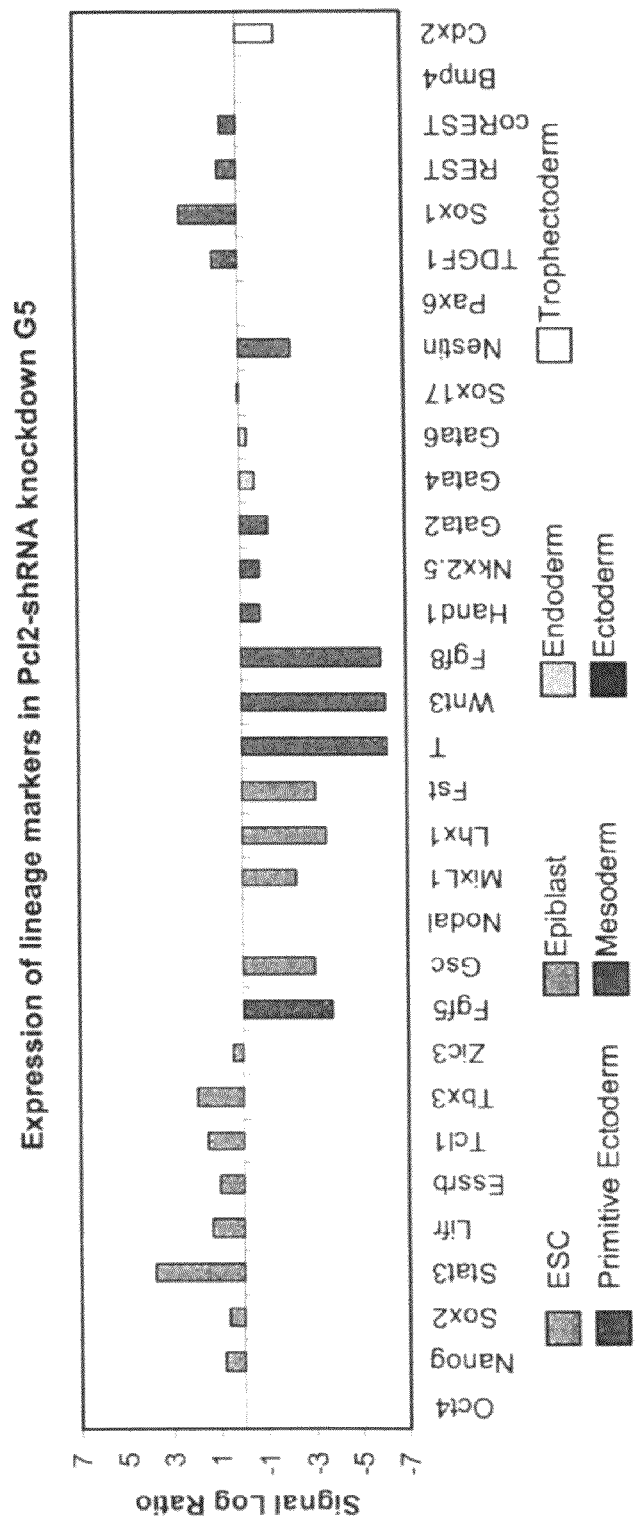

In addition, expression microarray analysis on control and Pcl2 shRNA clones was performed (FIG. 5). Gene ontology (GO) analysis showed that down-regulated genes were involved in differentiation and development, specifically heart development (FIG. 5B). Markers of undifferentiated ESCs were up-regulated and markers of epiblast and mesoderm were dramatically down-regulated (FIG. 5C) suggesting that Pcl2 may have a role in mesoderm development.

Finally, a colony forming assay followed by alkaline phosphatase (ALP) staining was performed to measure the ability of the Pcl2 shRNA cells to maintain the morphology of undifferentiated ESCs. In this assay, cells were plated at low density (500 cells/well of a 12-well dish) and grown for 5 days in LIF-containing media. They were then fixed and stained for ALP and the number of undifferentiated colonies was counted. An undifferentiated colony stains dark red and has a rounded morphology while a differentiated colony stains light yellow, the colony begins to flatten and individual cells spread outward and adopt various different morphologies. In this assay, Pcl2 shRNA cells formed undifferentiated colonies with much greater efficiency than controls (up to 95% compared to 40% of controls were undifferentiated) (FIG. 4D).

These data indicate that reduced Pcl2 expression results in an increase in OCT4, NANOG and SOX2 protein in the undifferentiated state and a maintenance of the level of these proteins during the early stages of commitment. In addition, Pcl2 shRNA cells form highly and homogenously undifferentiated colonies when cultured in self-renewing conditions.

Down-Regulation of Pcl2 Leads to Impaired Differentiation Capacity and Altered Onset of Key Developmental Regulators Monolayer differentiation strategies are ideal for studying the early time points of ESC commitment to differentiation; however, they can only be maintained for 5 days before the cells become overgrown. To study later time points, Pcl2 shRNA and control cells were used to form embryoid bodies (EBs) in suspension culture. Using this strategy, EBs were cultured for up to 25 days. Gene expression changes during EB formation recapitulate gene expression changes during early development and thus, this is a suitable model system for studying the effects of Pcl2 depletion on early development. There was a striking difference in appearance between Pcl2 shRNA and control EBs after 25 days in culture. Control EBs had undergone cavitation and formed cystic bodies, expelling the dead cells from the centre of the spherical structure. Pcl2 shRNA EBs remained a small, tightly compacted group of cells. Since earlier data suggested that Pcl2 shRNA clones maintained an undifferentiated, self-renewal population of cells, even in the absence of LIF, 25 day EBs were trypsinized and resuspended as a single-cell suspension. Cells were plated on a 10-cm gelatin-coated tissue culture dish in +LIF conditions. After three days they were fixed and stained for ALP. Control EBs formed no ALP positive colonies after 25 days of differentiation, however Pcl2 shRNA EBs formed 1000s of darkly stained colonies with undifferentiated morphology.

Figure 4:
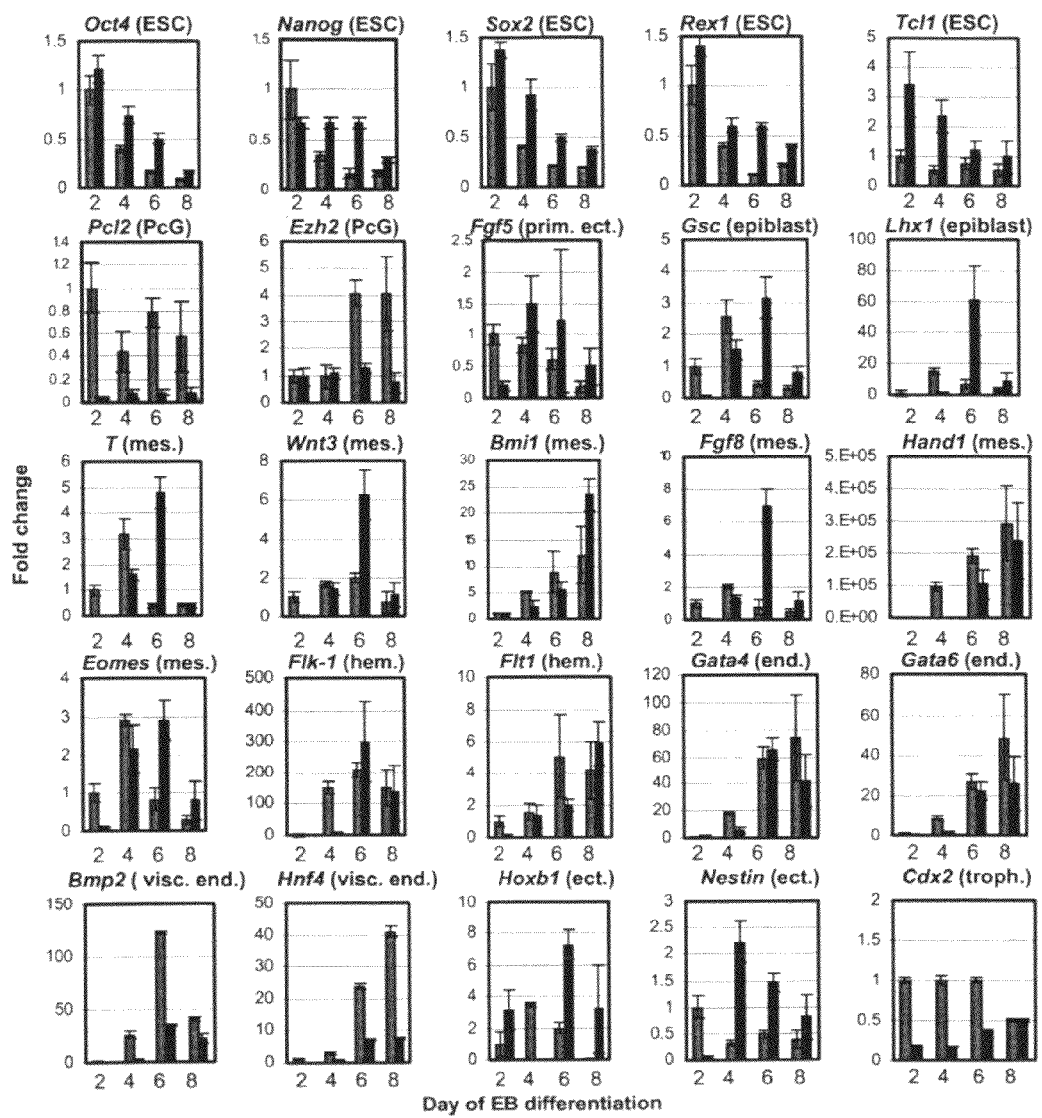
FIG. 4 is quantitative real-time PCR data using primers for twenty differentiation markers for different lineages. Cells were differentiated as EBs in suspension for eight days with RNA harvested on day 2, 4, 6 and 8. Pcl2 shRNA clone expression is in blue, control expression is in red. Data is represented as a fold change above or below the control expression on day 2 of differentiation.

To study gene expression changes throughout EB formation, RNA was extracted for qPCR studies at days 2, 4, 6 and 8. Supporting earlier data indicating that self-renewal markers were up-regulated in the undifferentiated Pcl2 shRNA cells, transcripts for Oct4, Nanog, Sox2, Rex1 and Tcl1 were elevated in Pcl2 shRNA EBs for several days after they had been down-regulated in control EBs (FIG. 4). At early time-points, expression of primitive ectoderm (Fgf5), epiblast (Gsc, Lhx1) and mesoderm markers (T, Wnt3, Bmi1, Fgf8, Hand1, Flk-1 and Flt1) were repressed to a greater extent than in controls. Their peak activation is greater than controls but delayed by two days. Interestingly, this delay corresponds with the delayed down-regulation of PRC2 components and the time frame during which 3me-H3K27 is artificially elevated in Pcl2 shRNA cells. In contrast, expression of early endoderm markers Gata4 and Gata6 are not significantly altered. Later markers of visceral endoderm Bmp2 and Hnf4 remain greatly reduced in Pcl2 shRNA EBs compared to controls throughout the time-course. Interestingly, BMP2 signaling has been shown to be responsible for the EB cavitation, which did not occur in the Pcl2 shRNA EBs. Expression of ectodermal markers Nestin and Hoxb1 showed the same delay and over-activation as mesodermal markers but trophectodermal marker Cdx2 was not significantly affected.

To study the ability of Pcl2 shRNA cells to differentiate towards neuroectodermal lineages, Pcl2 shRNA and control cells were plated on 0.1% gelatin at low density in N2B27 media (as described in Ying et al., 2003b, the relevant contents of which are incorporated herein by reference). This is a selective assay in which all cells that are not becoming neural will die and lift off the plate. After five days, cells were fixed and stained with Nestin, a marker for a neural precursor cell, and OCT4. Control cells readily expressed Nestin at 5 days, while the majority of Pcl2 shRNA cells had lifted off the plate and no Nestin expression could be detected in the remaining cells. Control cells had flattened and spread out, acquiring several different morphologies, however the remaining Pcl2 shRNA cells were still arranged in ESC-like colonies. Some of the control cells stained weakly for OCT4, as was expected, since OCT4 diminishes slowly in differentiating cells. In contrast, Pcl2 shRNA cells, which were still arranged in ESC colonies, expressed high levels of OCT4 protein. Thus, it appears that in monolayer culture, Pcl2 shRNA cells are unable to acquire the neuroectodermal fate.

Together these data suggest that Pcl2 is critically involved in the early commitment and differentiation of ESCs. The epigenetic changes resulting from inappropriate Pcl2 expression cause delayed activation of mesodermal and ectodermal markers. In addition, Pcl2 shRNA cells appear unable to progress to terminal differentiation of some cell types while at the same time retaining a population of self-renewing ESC-like cells which are insensitive to differentiation cues, resulting in tumour formation in vivo.

Direct Targets of PCL2 are Oncogenes and Cell Cycle Regulators

Figure 6:
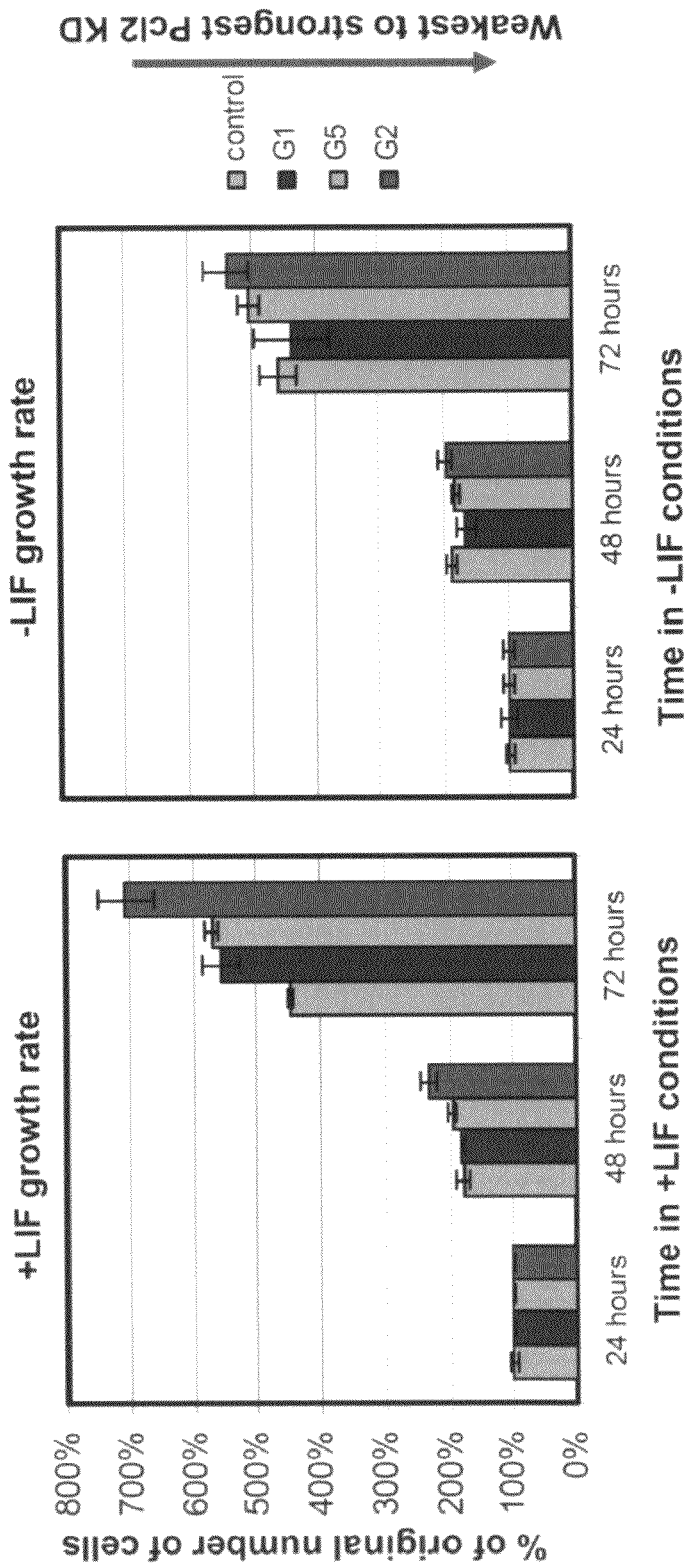
FIG. 6 represents the number of cells counted 24, 28 and 72 hours after plating both control and Pcl2 shRNA cells. Increased Pcl2-knockdown results in increased proliferation of ESCs in +LIF conditions. Knockdown clones are arranged in order of increasing knockdown.

To determine whether Pcl2 expression levels could alter cell cycle, proliferation rates were tracked (cell numbers at 24 hours, 48 hours and 72 hours post-plating) in both +LIF and −LIF conditions. In +LIF conditions, cell numbers were increased in direct correlation with the level of Pcl2 knockdown (FIG. 6, left panel). By 72 hours, all the knockdown clones demonstrated increased proliferation (560-700% of the cells plated compared to 450% for control). Although this trend appeared in the −LIF conditions, it was not as dramatic (cell number increase in the control is 450% compared to 550% for G2 clone). This suggests that PCL2 keeps proliferation in check in undifferentiated stem cells.

Figure 5D:
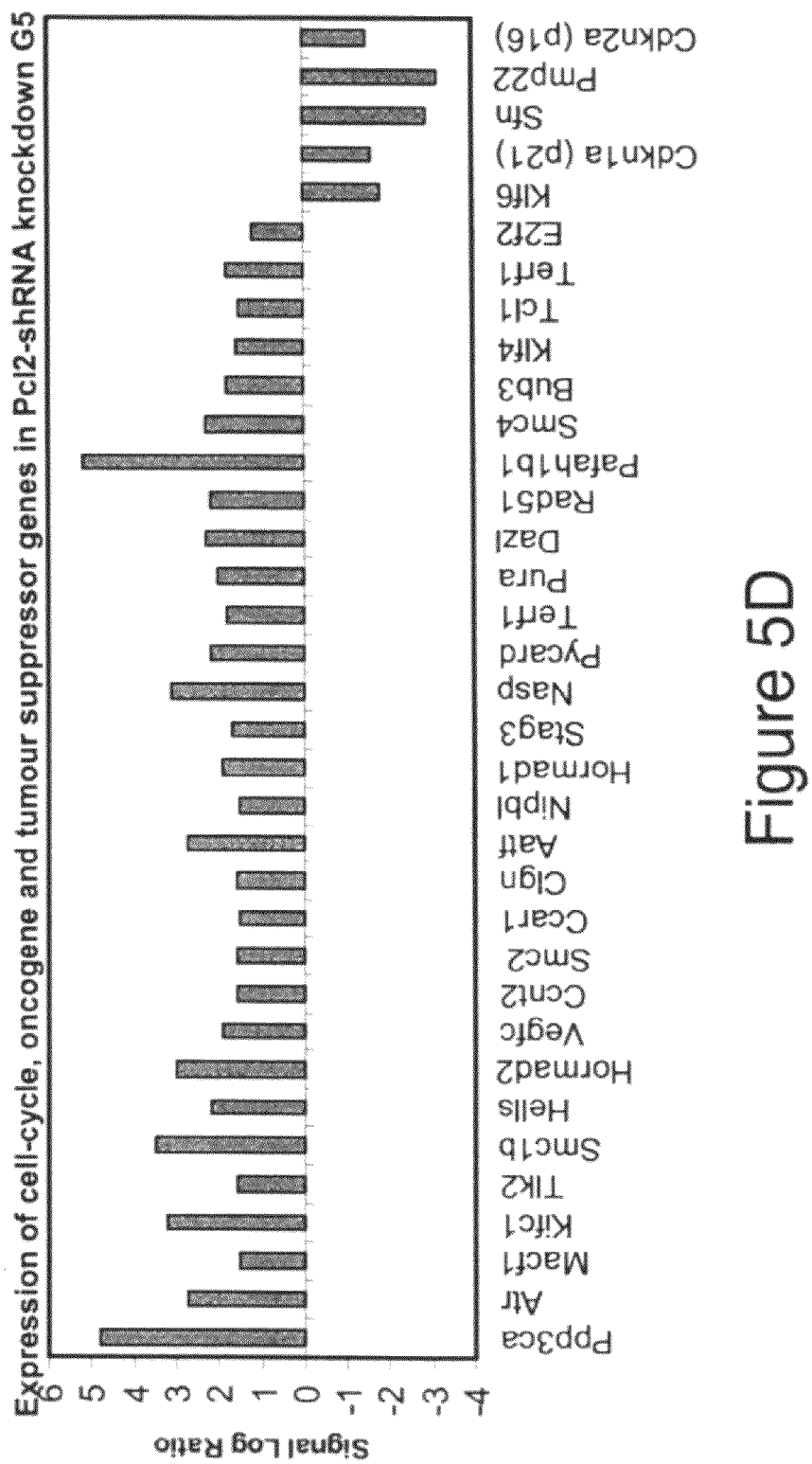

In addition, GO analysis of Pcl2 knockdown microarray data revealed that Pcl2 knockdowns showed an up-regulation of genes involved in positively regulating cell cycle and oncogenes such as Klf4 and Tcl1 (FIG. 5A & 5D). Down-regulated genes included several tumour suppressors such as Klf6 and negative regulators of cell cycle such as p21 and p16 (FIG. 5D). This has critical implications for tumour progression and indicates that PCL2 acts as a tumour-suppressor.

Taken together, PCL2 appears to play a role in chromatin remodeling through its interaction with PRC2 as well as in cell cycle progression, both important processes controlling stem cell fate and also tumorigenesis and cancer progression.

A Mouse Model of Pcl2 has Multiple Developmental Defects and is Pre-Leukemic

Gene trapping mESCs generates random loss-of-function mutations, identified by sequence tags as described in Stanford et al. 2001. Nat Rev Genet 2, 756-768, the relevant contents of which are incorporated herein by reference. Pcl2 expression is highest during embryogenesis but is also expressed in several adult tissues including bone marrow, spleen and thymus. A gene trap strain ($Pcl2^{GT}$) from the CMHD gene trap resource was generated. Homozygous $Pcl2^{GT}$ mice demonstrate pleiotropic defects, including superficial lymph node enlargement bordering on lymphoma, situs inversus, absence of subcutaneous fat, hair cycling defects, severe growth impairment and death by 3 months of age. The "pre-lymphoma" pathology assessment and bone marrow expression prompted analysis of Pcl2 expression during hematopoietic ontogeny and it was found that it was specifically expressed in cycling hematopoietic stem cells (HSCs) and some multipotent progenitors.

We claim:

1. A method of inhibiting, or at least reducing, blockage of cell differentiation in target murine embryonic stem cells comprising the step of increasing the level of polycomb-like protein PCL2 by enhancing Pcl2 expression in the target stem cells to a level that normally exists in the target stem cells to inhibit or at least reduce blockage of cell differentiation, wherein Pcl2 expression is increased by administration to the target stem cells of functional Pcl2 gene.

2. The method of claim 1, wherein Pcl2 expression is increased in cells in vitro.

3. The method of claim 1, wherein Pcl2 expression is increased to a level of about 1.4 of the average expression level of Pcl2 in tissue.

* * * * *